US008604213B2

(12) United States Patent
Dimagno

(10) Patent No.: US 8,604,213 B2
(45) Date of Patent: Dec. 10, 2013

(54) FLUORINATION OF AROMATIC RING SYSTEMS

(75) Inventor: Stephen Dimagno, Lincoln, NE (US)

(73) Assignee: Nutech Ventures, Lincoln, NE (US)

( * ) Notice: Subject to any disclaimer, the term of this patent is extended or adjusted under 35 U.S.C. 154(b) by 46 days.

(21) Appl. No.: 13/125,209

(22) PCT Filed: Oct. 20, 2009

(86) PCT No.: PCT/US2009/061308
§ 371 (c)(1),
(2), (4) Date: Jul. 6, 2011

(87) PCT Pub. No.: WO2010/048170
PCT Pub. Date: Apr. 29, 2010

(65) Prior Publication Data
US 2012/0004417 A1    Jan. 5, 2012

Related U.S. Application Data

(60) Provisional application No. 61/107,156, filed on Oct. 21, 2008, provisional application No. 61/236,037, filed on Aug. 21, 2009.

(51) Int. Cl.
*C07D 213/08* (2006.01)
*C07C 227/16* (2006.01)

(52) U.S. Cl.
USPC ........ 546/330; 548/202; 548/346.1; 558/268; 558/425; 560/25; 562/446

(58) Field of Classification Search
None
See application file for complete search history.

(56) References Cited

U.S. PATENT DOCUMENTS

| | | | |
|---|---|---|---|
| 8,377,704 | B2 | 2/2013 | DiMagno et al. |
| 2005/0226776 | A1 | 10/2005 | Brady et al. |
| 2006/0120958 | A1 | 6/2006 | Brady et al. |
| 2006/0128031 | A1 | 6/2006 | Robotti et al. |
| 2006/0292060 | A1 | 12/2006 | Wadsworth et al. |
| 2007/0092441 | A1 | 4/2007 | Wadsworth et al. |
| 2009/0286992 | A1 | 11/2009 | Carroll et al. |
| 2011/0091982 | A1 | 4/2011 | Dimagno et al. |
| 2011/0144344 | A1 | 6/2011 | Woodcraft |
| 2011/0190505 | A1 | 8/2011 | Dimagno |
| 2011/0313170 | A1 | 12/2011 | Dimagno |

FOREIGN PATENT DOCUMENTS

| | | |
|---|---|---|
| WO | WO 03/002157 | 1/2003 |
| WO | WO 2005/021472 | 3/2005 |
| WO | WO 2005/061415 | 7/2005 |
| WO | WO 2005/097713 | 10/2005 |
| WO | WO 2008/082695 | 7/2008 |
| WO | WO 2010/008522 | 1/2010 |
| WO | WO 2010/048170 | 4/2010 |

OTHER PUBLICATIONS

Zhang et al., "A practical route for synthesizing a PET ligand containing [18F] flourobenzene using reaction of diphenyliodonium salt with [18F]F-," *Tetrahedron Letters*, Nov. 7, 2007, 48(49):8632-8635.
Grushin et al., "Arylation of anions by diarylhalonium fluoroborates under conditions of interphase catalysis," *Russian Chemical Bulletin of the Academy of Sciences of the USSR*, Jan. 1, 1984, 33(10):2130-2135.
Van Der Puy et al., "Conversion of diaryliodonium salts to aryl fluorides," *Journal of Fluorine Chemistry*, Jan. 1, 1982, 21:385-392.
Wang et al., "Improved arene fluorination methodology for 1(111) salts," *Organic Letters*, Aug. 6, 2010, 12(15):p. 3352-3355.
EP 09822555.0 Supplemental Search Report, completed Feb. 16, 2012, 9 pages.
Cai et al., "Chemistry with [18F]fluoride ion," *European Journal of Organic Chemistry*, 2008, 17:2853-2873.
Hansch et al., "A survey of Hammett substituent constants and resonance and field parameters," *Chem. Rev.*, 1991, 91(2):165-195.
Sánchez et al., "Regioselective functionalisation of nitrobenzene and benzonitrile derivatives via nucleophilic aromatic substitution of hydrogen by phosphorus-stabilized carbanions," *Tetrahedron*, 2006, 62:3648-3662.
Sun et al., "Fluoride relay: a new concept for the rapid preparation of anhydrous nucleophilic fluoride salts from KF," *Chemical Communications*, 2007, (5):528-529.
Authorized Officer Young Jin Kang, PCT/US2009/061308, International Search Report and Written Opinion of the International Searching Authority, mailed Apr. 30, 2010, 9 pages.
Authorized Officer Gijsbertis Beijer, PCT/US2009/061308, International Preliminary Report on Patentability, issued Apr. 26, 2011, 7 pages.
Abboud et al., "Hydrogen Bonding in the Gas Phase and in Solution. New Experimental Developments," *Quantitative Treatments of Solute/Solvent Interactions*, Polarizer and Murray Ed. Elsevier: Amsterdam, 1994, pp. 134-179.
Adams et al., "Nucleophilic routes to selectively fluorinated aromatics," *Chem. Soc. Rev.*, 1999,28:225-231.
Albrecht et al., "Structural Versatility of Anion—π Interactions in Halide Salts with Pentafluorophenyl Substituted Cations," *J. Am. Chem. Soc.*, 2008, 130:4600-01.
Al-Qahtani et al., "Palladium(II)-mediated 11C-carbonylative coupling of diaryliodonium salts with organostannanes. A new, mild and rapid synthesis of aryl [11C]ketones.," *J. of Chem Soc. Perkin Transactions 1*, 2000, 1033-1036.
Bailly et al., "Pentafluorophenyliodine(III) compounds. Part 3. (Pentafluorophenyl)iodine difluoride: alternative preparations, molecular structure, and properties," *Z Anorg. Allg. Chem.*, 2000, 626:1406-1413.
Bielawski et al., "High-yielding one-pot synthesis of diaryliodonium triflates from arenes and iodine or aryl iodides," *Chem. Commun.*, 2007, 2521-2523.
Biffinger et al., "The Polar Hydrophobicity of Fluorinated Compounds," *ChemBiochem*, 2004, 5:622-627.

(Continued)

*Primary Examiner* — Zinna Northington Davis
(74) *Attorney, Agent, or Firm* — Fish & Richardson P.C.

(57) ABSTRACT

This disclosure relates to reagents and methods useful in the synthesis of aryl fluorides, for example, in the preparation of $^{18}$F labeled radiotracers. The reagents and methods provided herein may be used to access a broad range of compounds, including aromatic compounds, heteroaromatic compounds, amino acids, nucleotides, and synthetic compounds.

37 Claims, 4 Drawing Sheets

(56) References Cited

OTHER PUBLICATIONS

Bini et al., "Development of Cation/Anion 'Interaction' Scales for Ionic Liquids through ESI-MS Measurements," *J. Phys. Chem. B*, 2007, 111(3):598-604.

Blondel et al., "Electron spectrometry at the µeV level and the electron affinities of Si and F," *J. Phys. B: At., Mol. Opt. Phys.*, 2001, 34:2757.

Boechat et al., "Fluorodenitrations using tetramethylammonium fluoride," *J. Chem. Soc., Chem. Commun.*, 1993, 921-922.

Cerioni et al., "Solution structure of bis(acetoxy)iodoarenes as observed by $^{17}$O NMR spectroscopy," *Tetrahedron Lett.*, 2004, 45:505-507.

Choudhury et al., "Crystal engineering via C-H F and C-H π interactions in two substituted indoles," *Acta Cryst.*, 2004, C60:o644.

Christe et al., "Quantitative Measure for the 'Nakedness' of Fluoride Ion Sources," *J. Am. Chem. Soc.*, 2003, 125:9457-9461.

Christe et al., "Syntheses, properties, and structures of anhydrous tetramethylammonium fluoride and its 1:1 adduct and trans-3-amino-2-butenenitrile," *J. Am. Chem. Soc.*, 1990, 112:7619-25.

Ciufolini et al., "Oxidative amidation of phenols through the use of hypervalent iodine reagents," *Development and applications. Synthesis*, 2007, 3759-3772.

Crivello, "A new visible light sensitive photoinitiator system for the cationic polymerization of epoxides," *J. Polym. Sci., Part A: Polym. Chem.*, 2009, 47:866-875.

Crivello, "Photoactivated cationic ring-opening frontal polymerization of oxetanes," *Polym. Prepr. (Am. Chem. Soc., Div. Polym. Chem.)* 2006, 47:208-209.

Curran, D. P. et al. "Experimental techniques in fluorous synthesis: A user's guide," *Comb. Chem.*, 2000, 327-352.

Darses et al., "Potassium organotrifluoroborates. New partners in palladium-catalyzed cross-coupling reactions.," *Eur. J. Org. Chem.*, 1999, 1875-1883.

Darses et al., "Potassium trifluoro(organo)borates: New perspectives in organic chemistry," *Eur. J. Org. Chem.*, 2003, 4313-4327.

Davies et al., "Ab initio and DFT computer studies of complexes of quaternary nitrogen cations: trimethylammonium, tetramethylammonium, trimethylethylammonium, choline and acetylcholine with hydroxide, fluoride and chloride anions," *Phys. Chem. Chem. Phys.*, 2003, 5:4533-4540.

DiMagno et al., "Facile Synthesis of meso-Tetrakis(perfluoroalkyl)porphyrins: Spectroscopic Properties and X-ray Crystal Structure of Highly Electron-Deficient 5,10,15,20-Tetrakis(heptafluoroproyl)porphyrin," *J. Org. Chem.*, 1994, 59:6943.

DiMagno et al., "The Strength of Weak Interactions: Aromatic Fluorine in Drug Design," *Curr. Top. Med. Chem.*, 2006, 6:1473-1482.

Dohi et al., "A chiral hypervalent iodine(III) reagent for enantioselective dearomatization of phenols," *Angew. Chem. Int. Ed. Engl*, 2008, 47,:3787-90.

Ermert et al, "Comparison of pathways to the versatile synthon of no-carrier-added 1-bromo-4-[18F]fluorobenzene," Journal of Labelled Compounds & Radiopharmaceuticals 2004, 47, 429-441.

Fernandez et al., "Multinuclear PG SE Diffusion and Overhauser NMR Studies on a Variety of Salts in THF Solution," *Inorg. Chem.*, 2005, 44:5509-5513.

Frohn et al., "Preparation of polyfluorinated cycloalk-1-enyl-, alk-l-enyl-, and alkyliodine tetrafluorides using XeF2 in the presence of appropriate Lewis acids as fluorooxidant," *J. Fluorine. Chem.*, 2005, 126:1036-1043.

Giroldo et al., "An Unusually Fast Nucleophilic Aromatic Displacement Reaction: The Gas-Phase Reaction of Fluoride Ions with Nitrobenzene," *Angew Chem. Int. Ed.*, 2004, 43:3588-3590.

Gnann et al., "Naked Fluoride Ion Sources: Synthesis, Characterization, and Coupling Reaction of 1-Methylhexamethylenetetramine Fluoride," *J. Am. Chem. Soc.*, 1997, 119:112-115.

Hof et al., "A Weak Attractive Interaction between organic Fluorine and an Amide Group," *Angew. Chem. Int. Ed.*, 2004, 43:5056-5059.

Hossain et al., "Reaction of iodoarenes with potassium peroxodisulfate/trifluoroacetic acid in the presence of aromatics. Direct preparation of diaryliodonium triflates from iodoarenes," *Tetrahedron*, 2006, 62:6955-6960.

Huang et al., "Synthesis of ether-linked fluorocarbon surfactants and their aggregational properties in organic solvents," *Journal of Colloid and Interface Science*, 2004, 272:457-464.

Kang et al., "Palladium-catalyzed coupling and carbonylative coupling of silyloxy compounds with hypervalent iodonium salts," *Tetrahedron Lett.*, 1997, 38:1947-1950.

Kang et al., "Palladium-Catalyzed Cross-Coupling of Organoboron Compounds with Iodonium Salts and Iodanes," *J. Org. Chem.*, 1996, 61:4720-4724.

Kazmierczak et al., "A simple, two-step conversion of various iodo arenes to (diacetoxyiodo) arenes with chromium(VI) oxide as the oxidant," *Synthesis*, 1998, 1721-1723.

Kazmierczak et al., "Syntheses of (diacetoxyiodo)arenes or iodylarenes from iodoarenes, with sodium periodate as the oxidant," *Molecules*, 2001, 6:881-891.

Ko et al., "Fluorous-Based Carbohydrate Microarrays," *J. Am. Chem. Soc.* 2005, 127, 13162-13163.

Kornath et al., "Tetramethylphosphonium Fluoride: 'Naked' Fluoride and Phosphorane," *Inorg. Chem.*, 2003, 42:2894-2901

Kraszkiewicz et al., "Facile syntheses of symmetrical diaryliodonium salts from various arenes, with sodium metaperiodate as the coupling reagent in acidic media," *Synthesis*, 2008, 2373-2380.

Lubinkowski et al., "Reactions of diaryliodonium fluoroborates with inorganic anions," *J. Org. Chem.*, 1978, 43:2432-2435.

Lummis et al., "A Cation-π Binding Interaction with a Tyrosine in the Binding Site of the $GABA_c$ Receptor," *Chemistry & Biology*, 2005, 12:993-997.

McMillen et al., "Hydrocarbon Bond Dissociation Energies," *Ann. Rev. Phys. Chem.*, 1982, 33:493 (abstract only).

McKillop et al., "Further functional-group oxidations using sodium perborate," *Tetrahedron*, 1989, 45:3299-306.

Moore et al., "Hypervalent iodine-promoted phenolic oxidations: Generation of a highly versatile o-quinone template," *Chemtracts*, 2002, 15:74-80.

Moriarty et al., "Oxidation of phenolic compounds with organohypervalent iodine reagents," *Org. React.*, 2001, 57:327-415.

Okayama et al., "Solvolysis of Cyclohexenyliodonium Salt, a New Precursor for the Vinyl Cation: Remarkable Nucleofugality of the Phenyliodonio Group and Evidence for Internal Return from an Intimate Ion-Molecule Pair," *J. Am. Chem. Soc.*, 1995, 117:3360-7.

Olsen et al., "A Fluorine Scan of Thrombin Inhibitors to Map the Fluorophilicity/Fluorophobicity of an Enzyme Active Site: Evidence for CF•••C¼OInteractions," *Angew Chem.*, 2003, 115:2611.

Padelidakis et al., "Synthesis and characterization of 2,6-difluorophenyliodine(III) derivatives," *J. Fluorine Chem.*, 1999, 99:9-15.

Page et al., "Simple direct synthesis of [bis(trifluoroacetoxy)iodo]arenes," *Synthesis*, 2006, 3153-3155.

Pearson et al., "Nucleophilic reactivity constants toward methyl iodide and trans-dichlorodi (pyridine)platinum(II)," *J. Am. Chem. Soc.*, 1968, 90:319-326.

Pike et al, "Reactions of cyclotron-produced [$^{18}$F]fluoride with diaryliodonium salts—a novel single-step route to no-carrier-added [$^{18}$F]fluoroarenes," *Journal of the Chemical Society, Chemical Communications*, 1995, 2215-2216.

Plenio et al., "The Coordination Chemistry of Fluorocarbons: Difluoro-m-cyclophance-Based Fluorocryptands and Their Group I and II Metal Ion Complexes," *Inorg. Chem.*, 1997, 36:5722.

Quideau et al., "Chemical and electrochemical oxidative activation of arenol derivatives for carbon-carbon bond formation," *Curr. Org. Chem.*, 2004, 8:113-148.

Ross et al, "Nucleophilic 18F-Fluorination of Heteroaromatic Iodonium Salts with No-Carrier-Added [18F]Fluoride," Journal of the American Chemical Society, 2007, 129, 8018-8025.

Ryan et al., "Direct α-arylation of ketones: the reaction f cyclic ketone enolates with diphenyliodonium triflate," *Tetrahedron Lett.*, 1997, 38:5061-5064.

Schwesinger et al., "Stable Phosphazenium Ions in Synthesis—an Easily Accessible, Extremely Reactive 'Naked' Fluoride Salt," *Angew. Chem., Int. Ed. Engl.*, 1991, 30:1372.

Seppelt, "Does the Naked Fluoride Ion Exist?" *Angew. Chem., Int. Ed. Engl.*, 1992, 31:292.

(56) References Cited

OTHER PUBLICATIONS

Shah et al, "The synthesis of [18F]fluoroarenes from the reaction of cyclotron-produced [18F]fluoride ion with diaryliodonium salts," Journal of the Chemical Society, Perkins Transactions I 1998, 2043-2046.

Sharefkin et al., "Iodosobenzene Diacetate," *Org. Synth*,. 1963, 43, No pp. given.

Stoyanov et al., "An Infrared vNH Scale for Weakly Basic Anions. Implications for Single-Molecule Acidity and Superacidity," *J. Am. Chem. Soc.*, 2006, 128:8500-8508.

Sun et al., "A Method for Detecting Water in Organic Solvents," *Org. Lett.*, 2008, 10:4413-4416.

Sun et al., "Anhydrous Tetrabutylammonium Fluoride," *J. Am. Chem. Soc.*, 2005, 127:2050-2051.

Sun et al., "Competitive demethylation and substitution in N,N,N-trimethylanilinium fluorides," *J. Fluor. Chem.*, 2007, 128:806-812.

Sun et al., "Room-Temperature Nucleophilic Aromatic Fluorination: Experimental and Theoretical Studies," *Angew. Chem. Int. Ed.*, 2006, 45:2720-2725.

Sun et al., "Rapid Preparation of Fluorinated Aromatic Heterocycles," *ACS symposium series*, 2009, 1003:85-104.

Thalladi et al., "C-H•••F Interactions in the Crystal Structures of Some Fluorobenzenes," *J. Am. Chem. Soc.*, 1998, 120:8702-8710.

Thayer, "Fabulous Fluorine: Having fluorine in life sciences molecules brings desirable benefits, but the trick is getting it in place and making south-after building blocks," *C&E News*, 2006, 84:15-24.

Toba, "The design of photoinitiator systems," *J. Photopolym. Sci. Technol.*, 2003, 16:115-118.

Tohma et al., "Preparation and reactivity of 1,3,5,7-tetrakis[4-(diacetoxyiodo)phenyl]adamantane, a recyclable hypervalent iodine(III) reagent," *Angew. Chem., Int. Ed.*, 2004, 43:3595-3598.

Tsuzuki et al., "Magnitude and orientation dependence of intermolecular interaction between perfluoroalkanes: High level ab initio calculations of $CF_4$ and $C_2F_6$ dimers," *J. Chem. Phys.*, 2002, 116:3309-3315.

Tsuzuki et al., "Magnitude and orientation dependence of intermolecular interaction of perfluoropropane dimer studied by high-level ab initio calculations: comparison with propane dimer," *J. Chem. Phys.*, 2004, 121:9917-9924.

Tsuzuki et al., "Magnitude of Interaction between n-Alkane Chains and Its Anisotropy: High-Level ab Initio Calculations of n-Butane, n-Petane, and n-Hexane Dimers," *J. Phys. Chem. A*, 2004, 108:10311-10316.

Uyanik et al., "Enantioselective Kita Oxidative Spirolactonization Catalyzed by In Situ Generated Chiral Hypervalent Iodine(III) Species," *Angew. Chem., Int. Ed.*, 2010, 49, 2175-2177, S2175/1-S2175/79.

Wenthold et al., "Bond Dissociation Energies of $F_2^-$ and $HF_2^-$. A Gas-Phase Experimental and 62 Theoretical Study," *J. Phys. Chem.*, 1995, 99:2002-2005.

Ye et al., "Straightforward Syntheses of Hypervalent Iodine (III) Reagents Mediated by Selectfluor," *Org. Lett.*, 2005, 7:3961-3964.

Zhan et al., "Hydration of the Fluoride Anion: Structures and Absolute Hydration Free Energy from the First-Principles Electronic Structure Calculations," *J. Phys. Chem. A*, 2004, 108, 2020-2029.

Zhang et al., "Diels-Alder reaction and double phenylation in reaction of thiophenes with diphenyliodonium triflate," *Heterocycles*, 2004, 64:199-206.

Zhdankin et al., "Chemistry of Polyvalent Iodine," *Chem. Rev.*, 2008, 108:5299-5358.

Zhong et al., "From ab initio quantum mechanics to molecular neurobiology: A cation-π binding site in the nicotinic receptor," *PNAS*, 1998, 95:12088-12093.

Zielinska et al., "Easy preparation of (diacetoxyiodo)arenes from iodoarenes with sodium percarbonate as the oxidant," *Molecules*, 2002, 7:806-809.

Authorized Officer H. Sahagun Krause. Extended European Search Report in International Application No. 12185395.6, dated Nov. 16, 2012, 6 pages.

International Search Report and Written Opinion in International Application No. PCT/US2012/044954, mailed Feb. 13, 2013, 9 pages.

Comments Received from Third Party re Original Claims-Interpretations and Summaries, PCT/US2009/061308, Feb. 28, 2013, 488 pages.

Third Party Observation for Application No. EP20090822555, Feb. 28, 2013, 592 pages.

Observations related to Publication EP234997 and EP2537826, Feb. 28, 2013, 583 pages.

Beringer et al., "Diaryliodonium Salts. II. The Phenylation of Organic and Inorganic Bases," *Phenylation Org. Inorg. Bases*, Jun. 1953, 75:2708-2712.

Cai et al., "Chemistry with [$^{18}$F]fluoride ion," *Eur J Org Chem*, 2008, 17:2853-2873.

Carroll et al., "An ab initio and MNDO-d SCF-MO computational study of stereoelectronic control in extrusion reactions of $R_2$I-F iodine(III) intermediates," *J. Chem. Soc. Perkins Trans. 2*, 1999, 2707-2714.

Carroll et al., "Radical scavengers: A practical solution to the reproducibility issue in the fluoridation of diaryliodonium salts," *J Fluorine Chem.*, 2007, 128:127-132.

Carroll et al., "Studies towards 6-[$^{18}$F]Fluorodopa using Iodonium Salts: Preparation of 6-Fluoro-*m*-Tyramine," *J Label Compd Radiopharm.*, 2005, 48:519-546 (abstract).

Chen and Koser, "Direct and Regiocontrolled Synthesis of alph-Phyenyl Ketones from Silyl Enol Ethers and Diphenyliodonium Fluoride," *J. Org. Chem.*, 1991, 56:5764-5767.

Conway et al., "Iodonium Chemistry: Scope and Selectivity in Aromatic Nucleophilic Labelling Reactions," *J Label Compd Radiopharm.*, 2005, 48:S193 (Abstract).

Ermert et al, "Comparison of pathways to the versatile synthon of no-carrier-added 1-bromo-4-[$^{18}$F]fluorobenzene," *J Labelled Compd Radiopharm*, 2004, 47:429-441.

Ermolenko et al., "Nucleophilic Substitution in Iodonium Derivatives of Indole," *Chem Heterocyclic Compounds*, Jul. 1978, 14(7):752-754.

Gail et al., "Direct N.C.A. $^{18}$F-Fluorination of Halo- and alkylarenes via corresponding diphenyloidonium salts," *J. Label. Compd. Radiopharm.* (*Symposium Abstracts*), 1997, 40:50-52.

Grushin et al., "Arylation of anions with diarylhalonium fluoroborates under conditions of interphase catalysis," *Bulletin of the Academy of Sciences of the UUSR. Division of Chemical Science, Consultants Bureau*, 1984, 33(10):2130-2135.

Grushin, "Carboranylhalonium Ions: From Striking Reactivity to a Unified Mechanistic Analysis of Polar Reactions of Diarylhalonium Compounds," *Acc. Chem. Res.*, 1992, 25:529-536.

Grushin et al., "Unified Mechanistic Analysis of Polar Reactions o fDiaryliodonium Salts," *J. Chem. Soc. Perkin Trans. 2*, 1992, 505-511.

Hostetler et al., "Synthesis of 2-[$^{18}$F]Fluoroestradiol, a Potential Diagnostic Imaging Agent for Breast Cancer: Strategies to Achieve Nucleophilic Substitution of an Electron-Rich Aromatic Ring with [$^{18}$F]F$^-$," *J. Org. Chem.*, 1999, 64:178-185.

Iwama et al., "Regiocontrolled Synthesis of Carbocycle-Fused Indoles via Arylation of Silyl Enol Ethers with *o*-Nitrophenylphenyliodonium Fluoride," *Organic Lett.*, 1999, 1(4):673-676.

Jang et al., "Nucleophilic Aromatic ($^{18}$F)Fluorination of Electron-Rich Aromatic System Using Iodonium Salt," *J. Label. Compd. Radiopharm.*, 2007, 50:S210 (abstract).

Lubinkowski et al., "Reactions of Diaryliodonium Salts with Sodium Alkoxides," *J. Org. Chem.*, 1975, 40(21):3010-3015.

Martín-Santamaría et al., "Fluoridation of heteroaromatic iodonium salts—experimental evidence supporting theoretical prediction of the selectivity of the process," *Chem. Commun.*, 2000, 649-650.

Merritt et al., "Diaryliodonium Salts: A Journey from Obscurity to Fame," *Angew. Chem., Int. Ed.*, 2009, 48:9052-9070.

Miller et al., "Synthesis of $^{11}$C, $^{18}$F, $^{15}$O, and $^{13}$N Radiolabels for Positron Emission Tomography," *Angew. Chem. Int. Ed.*, 2008, 47:8998-9033.

Oh et al., "Highly Efficient Arylation of Malonates with Diaryliodonium Salts," *J. Org. Chem.*, 1999, 64:1338-1340.

(56) References Cited

OTHER PUBLICATIONS

Pike et al, "Reactions of cyclotron-produced [$^{18}$F]fluoride with diaryliodonium salts—a novel single-step route to no-carrier-added [$^{18}$]fluoroarenes," *J Chem Soc, ChemCommun*, 1995, 2215-2216.

Ross et al, "Nucleophilic $^{18}$F-Fluorination of Heteroaromatic Iodonium Salts with No-Carrier-Added [$^{18}$F]Fluoride," *J Am Chem Soc*, 2007, 129:8018-8025.

Ross et al., "N.C.A. $^{18}$F-Fluorination of Various Arenes via Aryl(2-Thienyl)Iodonium Salts," *J Label Compd Radiopharm.*, 2005, 48:S153 (Abstract).

Ross, "Direct no-carrier added 18F-labelling of arenes via nucleophilic susbtitution on aryl(2)-thienyl)iodonium salts," *Institute of Nuclear Medicine*, Julich, Germany, Thesis, 2006, 10 pages (table of contents).

Shah et al., "Synthesis of substituted diaryliodonium salts and investigation of their reactions with no-carrier-added [$^{18}$F]Fluoride," *J. Label. Compd. Radiopharm. (Symposium Abstracts)*, 1997, 40:65-67.

Shah et al, "The synthesis of [$^{18}$F]fluoroarenes from the reaction of cyclotron-produced [$^{18}$F]fluoride ion with diaryliodonium salts," *J Chem Soc, Perkins Transactions I*, 1998, 2043-2046.

Stang and Zhdankin, "Organic Polyvalent Iodine Compounds," *Chem. Rev.*, 1996, 96:1123-1178.

Van Der Puy et al., "Conversion of diaryliodonium salts to aryl fluorides," *J Fluorine Chem*, 1982, 21:385-392.

Varvoglis et al., *Hypervalent Iodine in Organic Synthesis*, Academic Press 1997, 1 page (table of contents).

Varvoglis and Spyroudis, "Hypervalent Iodine Chemistry: 25 years of Development at the University of Thessaloniki," *SYNLETT*, Mar. 1998, 221-232.

Wirth and Hirt, "Hypervalent Iodene Compounds: Recent Advances in Synthetic Applications," *Synthesis*, 1999, 8:1271-1287.

Wirth, "Hypervalent Iodine Chemistry: Modern Developments in Organic Synthesis," Topics in Current Chem., 2003, 7 pages (table of contents).

Wust et al., "Synthesis of novel arylpyrazolo corticosteroids as potential ligands for imaging brain glucocorticoid receptors," *Steroids*, 2003, 68:177-191.

Wust et al., "Synthesis of $^{18}$F-labelled cyclooxygenase-2 (COX-2) inhibitors via Stille reaction with 4-[$^{18}$F]fluoroiodobenzene as radiotracers for positron emission tomography (PET)," *Org. Biomol. Chem.*, 2005, 3:503-507.

Wust and Kniess, "Synthesis of 4-[$^{18}$F]fluoroiodobenzene and its application in sonogashira cross-coupling reactions," *J Label Compd Radiopharm.*, 2003, 46:699-713.

Wust et al., "PET-Corticosteroids as potential ligands for mapping brain glucocorticoid receptors (GR)," *J Label Compd Radiopharm.*, 2001, 44:457-459.

Wust and Kniess, "No-carrier added synthesis of $^{18}$F-labelled nucleosides using Stille cross-coupling reactions with 4-[$^{18}$F]fluoroiodobenzene," *J Label Compd Radiopharm.*, 2004, 47:457-468.

Zhang et al., "A practical route for synthesizing a PET ligand containing [$^{18}$F] fluorobenzene using reaction of diphenyliodonium salt with [$^{18}$F]F$^-$," *Tetrahedron Letters*, 2007, 48(49):8632-8635.

Zhang et al., "Practical Synthesis of ($^{18}$F)Fluorobenzene starting from Phenyltributystanne," *J. Label. Compd. Radiopharm.*, 2007, 50:S152.

Kilbourn et al., "Fluorine—18 Labeling of Radiopharmaceuticals," *National Academy Press*, 1990, 37-40.

FLUORINATION OF AROMATIC RING SYSTEMS

CROSS-REFERENCE TO RELATED APPLICATIONS

This application is a National Stage application under 35 U.S.C. §371 and claims the benefit under 35 U.S.C. §119(a) of International Application No. PCT/US2009/061308, having an International Filing Date of Oct. 20, 2009, which claims priority to U.S. Provisional Applications Ser. Nos. 61/107,156, filed on Oct. 21, 2008, and 61/236,037, filed on Aug. 21, 2009, both of which are incorporated by reference in their entirety herein

FEDERALLY SPONSORED RESEARCH OR DEVELOPMENT

The U.S. Government has certain rights in this invention pursuant to Grant No. CHE-0717562 awarded by the National Science Foundation.

TECHNICAL FIELD

This disclosure relates to reagents and methods useful in the synthesis of aryl fluorides, for example, in the preparation of $^{18}$F labeled radiotracers. The reagents and methods provided herein may be used to access a broad range of compounds, including aromatic compounds, heteroaromatic compounds, amino acids, nucleotides, and synthetic compounds.

BACKGROUND

Aryl fluorides are structural moieties in natural products as well as a number of therapeutically important compounds, including positron emission tomography (PET) tracers and pharmaceuticals. Therefore methods and reagents for producing such aryl fluorides, for example efficient methods for producing aryl fluorides, are desirable.

SUMMARY

Provided herein are methods of preparing substituted aryl and heteroaryl ring systems using diaryliodonium compounds and intermediates. For example, diaryliodonium salts and diaryliodonium fluorides, as provided herein, can undergo decomposition to prepare an aryl fluoride.

For example, provided herein is a method for making a compound of Formula (1):

   (1)

wherein $Ar^2$ is an aryl or heteroaryl ring system; and X is a moiety wherein the pKa of the acid H—X is less than 12. In one embodiment, the method includes reacting in a polar solvent a compound MX, wherein M is a counter ion and X is as defined in Formula (1), and a compound of Formula (2):

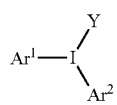   (2)

wherein $Ar^1$ is an electron rich aryl or heteroaryl ring system;
Y is a leaving group; and
$Ar^2$ and X are as defined above. Following reaction, the polar solvent can be removed from the reaction mixture and the remaining mixture can be combined with a nonpolar solvent and heated. In another embodiment, a solution comprising a nonpolar solvent, a compound MX, and a compound of Formula (2) can be heated to provide a compound of Formula (1).

In some embodiments, the nonpolar solution of the reaction mixture of MX and a compound of Formula (2) can be filtered prior to heating. The filtration step can remove any insoluble material (e.g., insoluble salts) that remain in the reaction mixture. In some embodiments, the solvent can be removed from the filtrate prior to heating (i.e., the residue can be heated neat).

In further embodiments, the nonpolar solution of the reaction mixture of MX and a compound of Formula (2) can be filtered prior to heating, the nonpolar solvent can be removed (e.g., by evaporation), and the heating of the sample can be performed in a different solvent.

In some embodiments, X can be chosen from halide, aryl carboxylate, alkyl carboxylate, phosphate, phosphonate, phosphonite, azide, thiocyanate, cyanate, phenoxide, triflate, trifluoroethoxide, thiolates, and stabilized enolates. For example, X can be chosen from fluoride, chloride, bromide, iodide, triflate, trifluoroacetate, benzoate, acetate, phenoxide, trifluoroethoxide, cyanate, azide, thiocyanate, thiolates, phosphates, and stabilized enolates. In some embodiments, X is fluoride. In some embodiments, X is a radioactive isotope, for example, X can be a radioactive isotope of fluoride (e.g., $^{18}$F).

The methods described herein can be used to prepare fluorinated aryl or heteroaryl ring systems (e.g., a radiolabeled fluorinated aryl or heteroaryl ring system). For example, provided herein is a method of preparing a compound of Formula (3):

   3 wherein $Ar^2$ is an aryl or heteroaryl ring system. In one embodiment, the method includes reacting in a polar solvent a compound MF, wherein M is a counter ion, and a compound of Formula (2), as described above. Following reaction, the polar solvent can be removed from the reaction mixture and the remaining mixture can be combined with a nonpolar solvent and heated. In another embodiment, a solution comprising a nonpolar solvent, a compound MF, and a compound of Formula (2) can be heated to provide a compound of Formula (3).

In some embodiments, the nonpolar solution of the reaction mixture of MF and a compound of Formula (2) can be filtered prior to heating. The filtration step can remove any insoluble material (e.g., insoluble salts) that remain in the reaction mixture. In some embodiments, the solvent can be removed from the filtrate prior to heating (i.e., the residue can be heated neat).

In further embodiments, the nonpolar solution of the reaction mixture of MF and a compound of Formula (2) can be filtered prior to heating, the nonpolar solvent can be removed (e.g., by evaporation), and the heating of the sample can be performed in a different solvent.

$Ar^1$ is an electron rich aryl or heteroaryl ring system. For example, $Ar^1$—H can be more easily oxidized than benzene. In some embodiments, the moiety $Ar^1$ can be substituted with at least one substituent having a Hammett $\sigma_p$ value of less than zero. For example, the substituent can be chosen from: —($C_1$-$C_{10}$)alkyl, —($C_1$-$C_{10}$)haloalkyl, ($C_2$-$C_{10}$)alkenyl, ($C_2$-$C_{10}$)

alkynyl, —O—($C_1$-$C_{10}$)alkyl, —C(O)—O—($C_1$-$C_{10}$)alkyl, aryl, and heteroaryl. In some embodiments, $Ar^1$ can be:

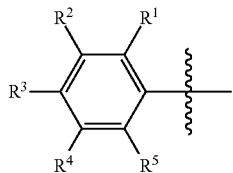

wherein $R^1$, $R^2$, $R^3$, $R^4$, and $R^5$ are independently chosen from: H, —($C_1$-$C_{10}$)alkyl, —($C_1$-$C_{10}$)haloalkyl, ($C_2$-$C_{10}$) alkenyl, ($C_2$-$C_{10}$)alkynyl, —O—($C_1$-$C_{10}$)alkyl, —C(O)—O—($C_1$-$C_{10}$)alkyl, aryl, and heteroaryl, or two or more of $R^1$, $R^2$, $R^3$, $R^4$, and $R^5$ come together to form a fused aryl or heteroaryl ring system.

$Ar^2$ is an aryl or heteroaryl ring system. In some embodiments, $Ar^2$ is chosen from a phenylalanine derivative, tyrosine derivative, typtophan derivative, histidine derivative, and estradiol derivative. In some embodiments, $Ar^2$ is chosen from:

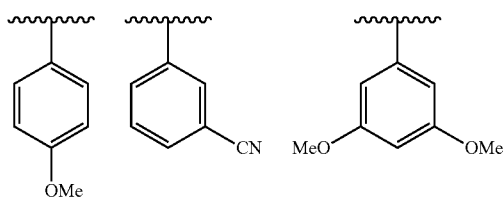

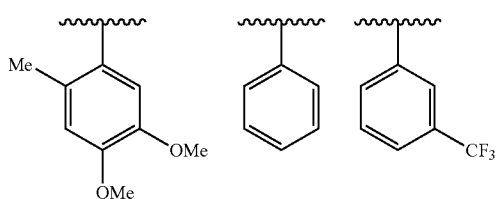

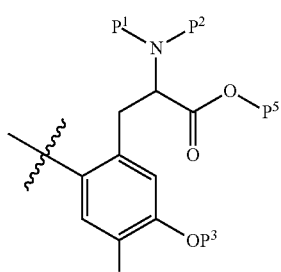

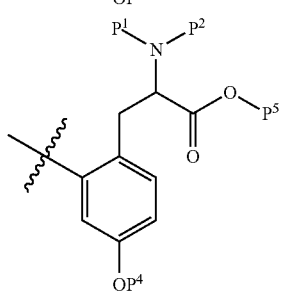

-continued

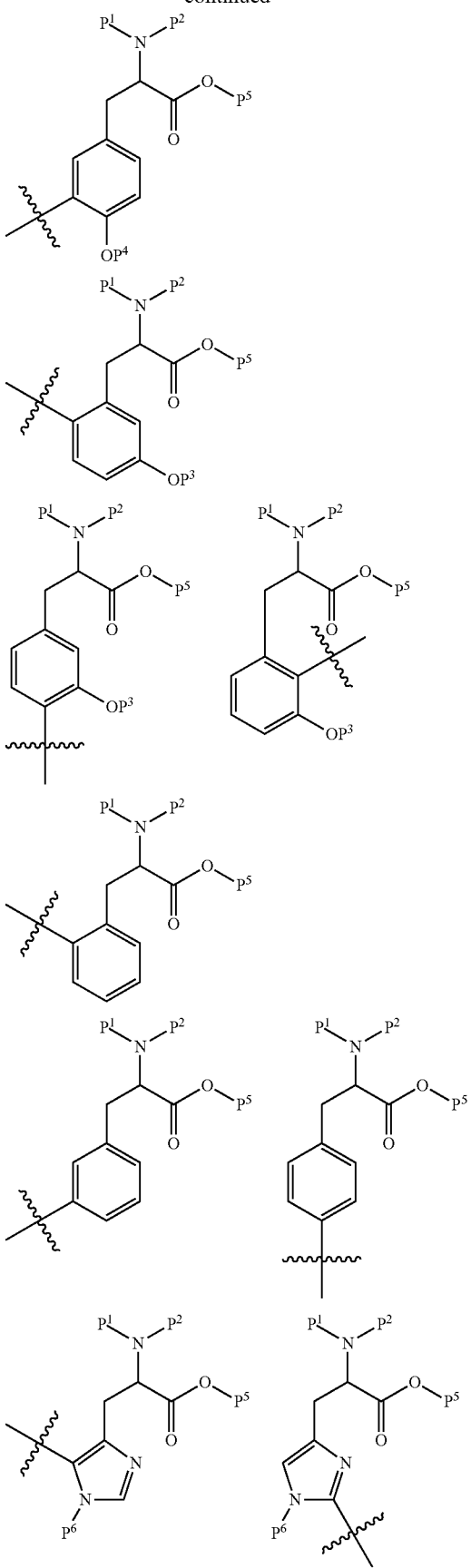

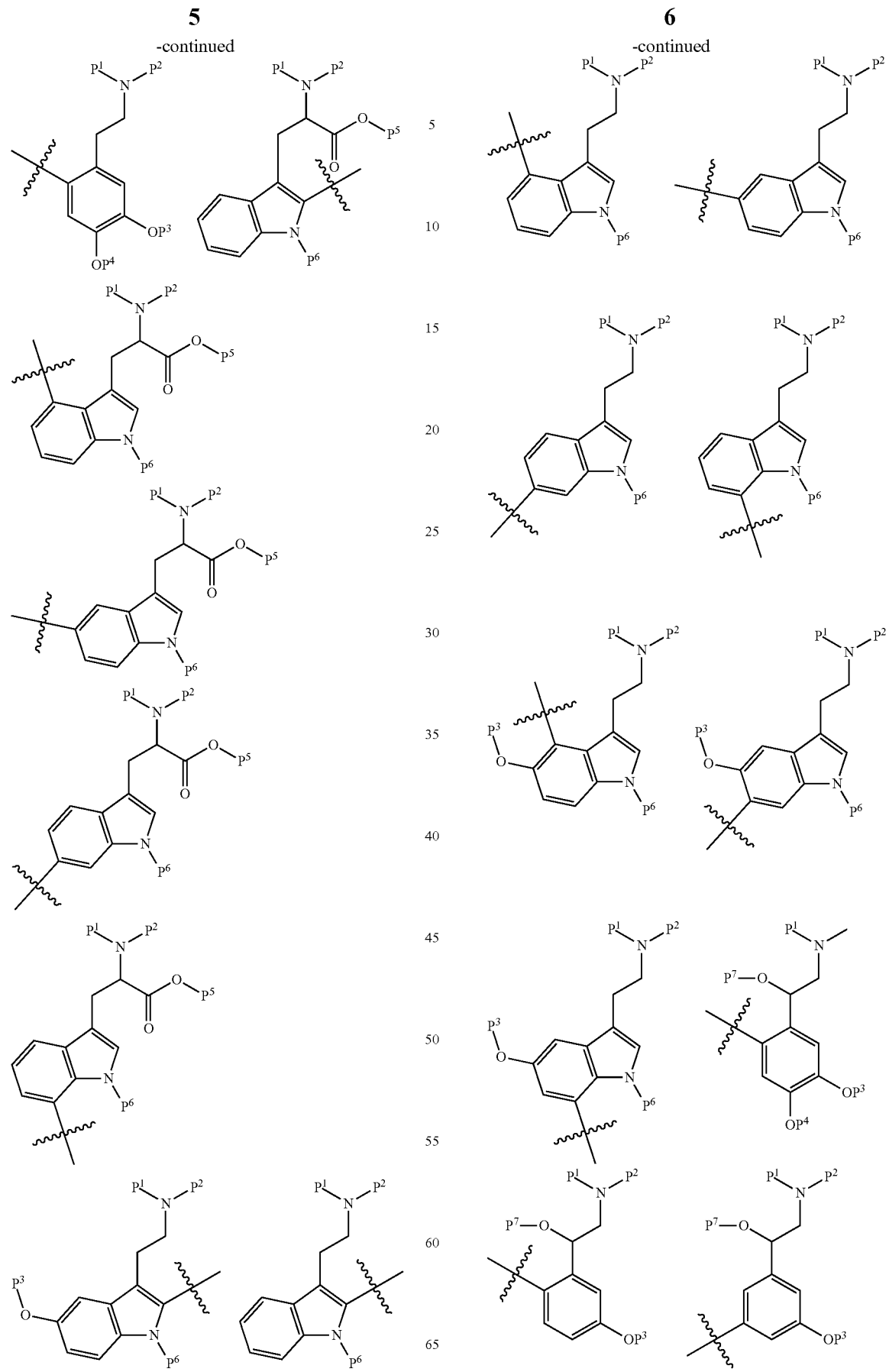

-continued

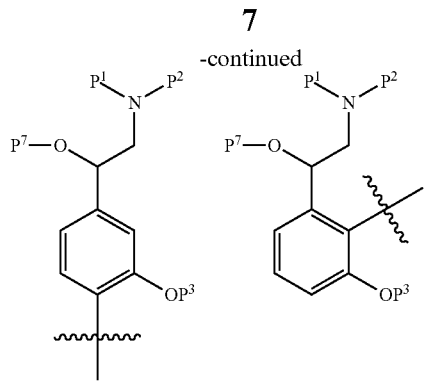

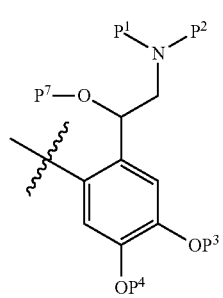

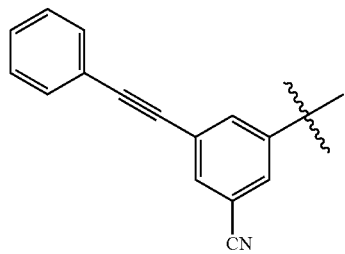

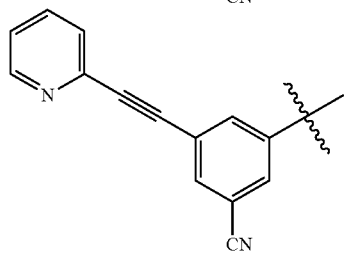

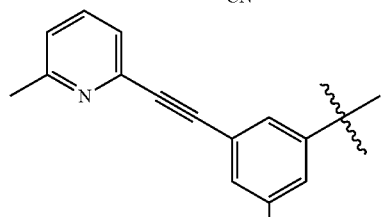

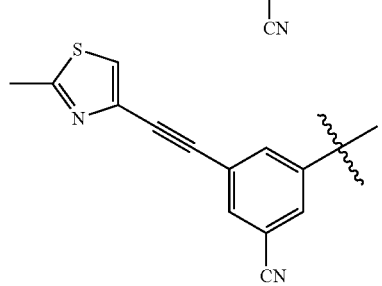

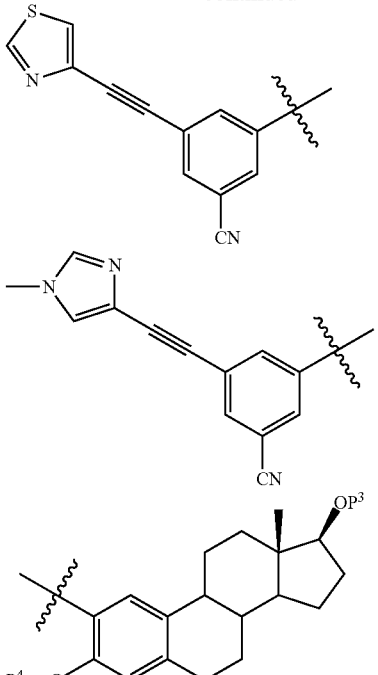

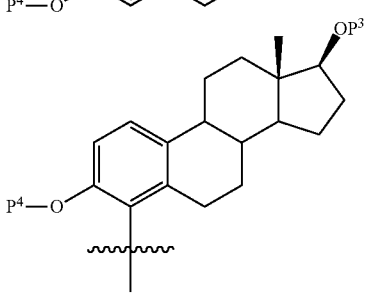

wherein each of $P^1$, $P^2$ and $P^6$ are independently a nitrogen protecting group, or $P^1$ and $P^2$ come together to form a single nitrogen protecting group; each of $P^3$, $P^4$, and $P^7$ are independently an alcohol protecting group, or $P^3$ and $P^4$ come together to form a single oxygen protecting group; and $P^5$ is a carboxylic acid protecting group.

Also provided herein is a method of making a compound of Formula (6):

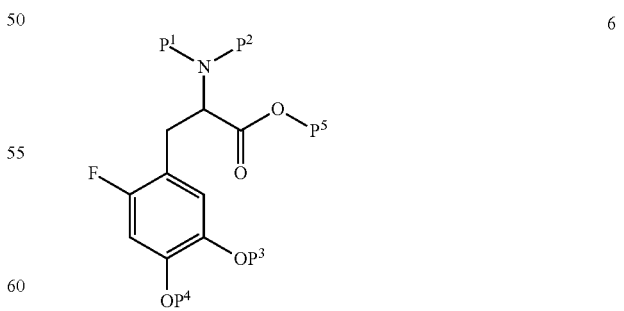

wherein each of $P^1$ and $P^2$ are independently a nitrogen protecting group, or $P^1$ and $P^2$ come together to form a single nitrogen protecting group; each of $P^3$, and $P^4$ are independently an alcohol protecting group, or $P^3$ and $P^4$ come together to form a single oxygen protecting group; and $P^5$ is a carboxylic acid protecting group. In one embodiment, the method includes reacting in a polar solvent a compound MF, wherein M is a counter ion, and a compound of Formula (7):

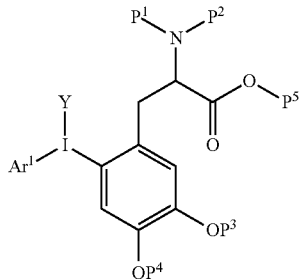

wherein Ar¹ is an electron rich aryl or heteroaryl ring system;
Y is a leaving group; and
$P^1$, $P^2$, $P^3$, $P^4$ and $P^5$ are as defined above. Following reaction, the polar solvent can be removed from the reaction mixture and the remaining mixture can be combined with a nonpolar solvent and heated. In another embodiment, a solution comprising a nonpolar solvent, a compound MF, and a compound of Formula (7) can be heated to provide a compound of Formula (6).

In some embodiments, the nonpolar solution of the reaction mixture of MF and a compound of Formula (7) can be filtered prior to heating. The filtration step can remove any insoluble material (e.g., insoluble salts) that remain in the reaction mixture. In some embodiments, the solvent can be removed from the filtrate prior to heating (i.e., the residue can be heated neat).

In further embodiments, the nonpolar solution of the reaction mixture of MF and a compound of Formula (7) can be filtered prior to heating, the nonpolar solvent can be removed (e.g., by evaporation), and the heating of the sample can be performed in a different solvent.

In the methods described above, Y can be any leaving group, for example, Y can be, for example, triflate, mesylate, nonaflate, hexaflate, tosylate, nosylate, brosylate, perfluoroalkyl sulfonate, tetraphenylborate, hexafluorophosphate, trifluoroacetate, tetrafluoroborate, perchlorate, perfluoroalkylcarboxylate, chloride, bromide, or iodide.

M can vary depending on the nature of the X moiety. In some embodiments, M can be potassium, sodium, cesium, complexes of lithium, sodium, potassium, or cesium with cryptands or crown ethers, tetrasubstituted ammonium cations, or phosphonium cations.

The nonpolar solvent used in the methods described herein can be, for example, benzene, toluene, o-xylene, m-xylene, p-xylene, ethyl benzene, carbon tetrachloride, hexane, cyclohexane, fluorobenzene, chlorobenzene, nitrobenzene, or mixtures thereof. In some embodiments, the nonpolar solvent comprises benzene. In some embodiments, the nonpolar solvent comprises toluene.

The polar solvent used in the methods described herein can be, for example, acetonitrile, acetone, dichloromethane, ethyl acetate, tetrahydrofuran, dimethylformamide, 1,2-difluorobenzene, benzotrifluoride or mixtures thereof.

Heating of the reaction mixture can include heating at a temperature ranging from about 25° C. to about 250° C. In some embodiments, the heating can occur for from about 1 second to about 25 minutes. In some embodiments, the heating is accomplished by a flash pyrolysis method, a conventional heating method, or by a microwave method.

In some embodiments, the compound of Formula (2) is chosen from:

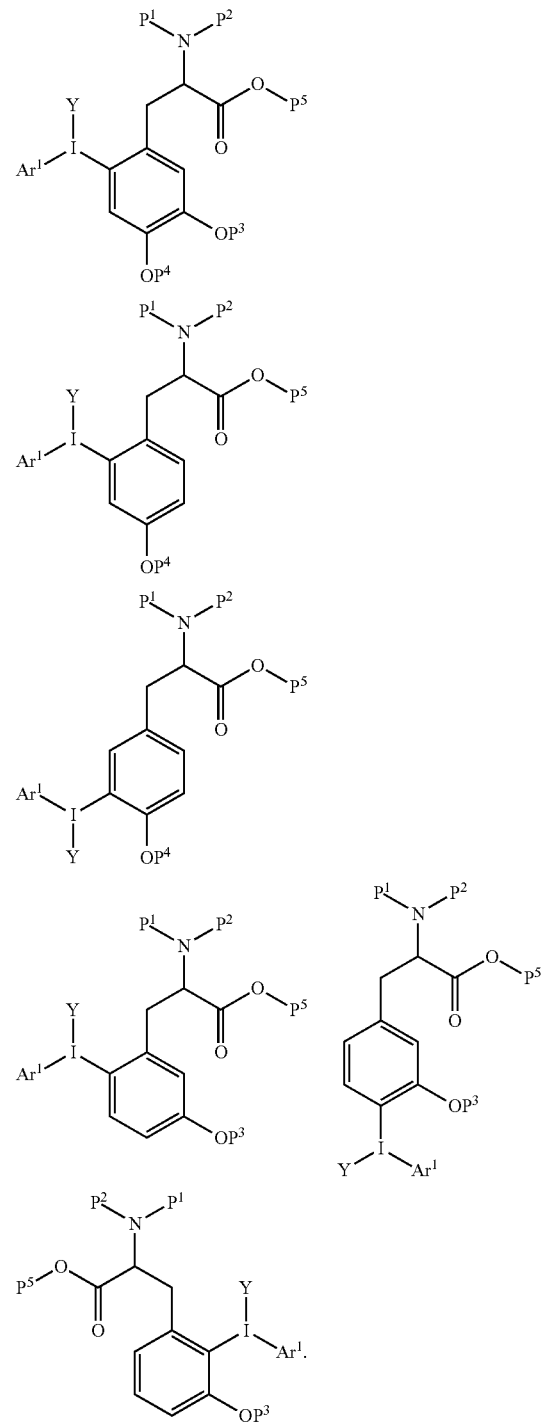

wherein each of $P^1$ and $P^2$ are independently a nitrogen protecting group, or $P^1$ and $P^2$ come together to form a single nitrogen protecting group; each of $P^3$, and $P^4$ are independently an alcohol protecting group, or $P^3$ and $P^4$ come together to form a single oxygen protecting group; and $P^5$ is a carboxylic acid protecting group. For example, the compound of Formula (2) can be:

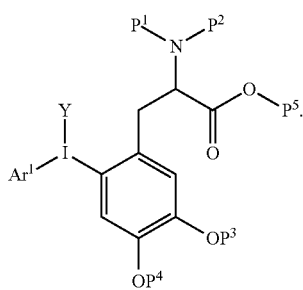

wherein each of $P^1$ and $P^2$ are independently a nitrogen protecting group, or $P^1$ and $P^2$ come together to form a single nitrogen protecting group; each of $P^3$, and $P^4$ are independently an alcohol protecting group, or $P^3$ and $P^4$ come together to form a single oxygen protecting group; and $P^5$ is a carboxylic acid protecting group. In some embodiments, the compound of Formula (2) can be:

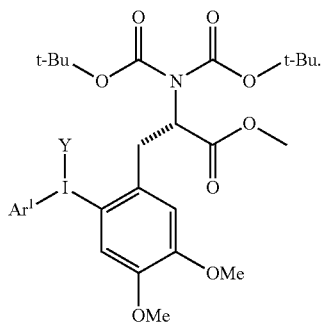

In some embodiments, the compound of Formula (2) can be:

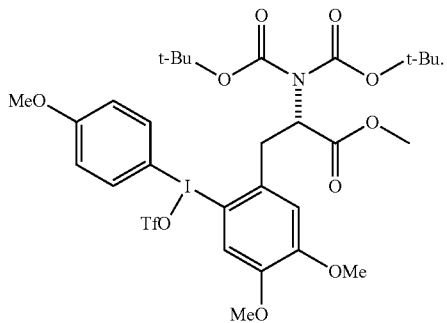 [SMILES: COC(=O)[C@H](Cc1cc(OC)c(OC)cc1I(OS(=O)(=O)C(F)(F)F)c1ccc(OC)cc1)N(C(=O)OC(C)(C)C)C(=O)OC(C)(C)C]

In some embodiments, the compound of Formula (2) is chosen from:

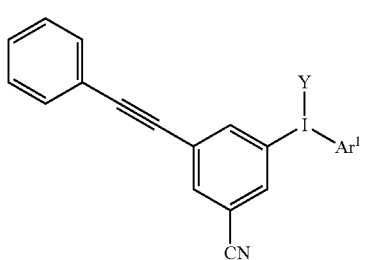

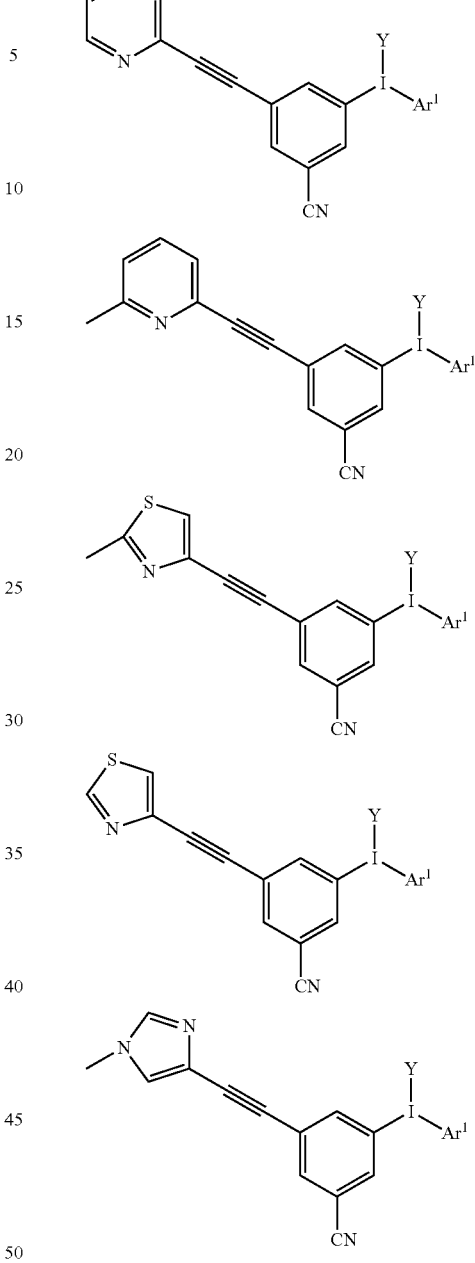

In some embodiments, the compound of Formula (2) is chosen from:

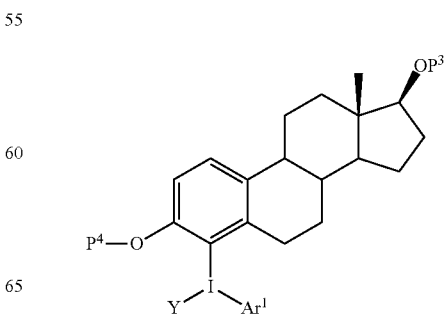

-continued

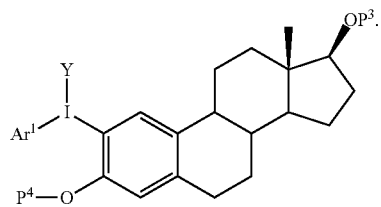

wherein each of P³ and P⁴ are independently an alcohol protecting group.

In some embodiments, the compound of Formula (1) or Formula (3) is chosen from:

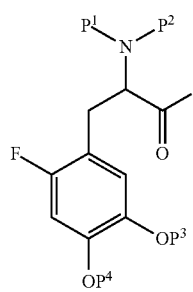 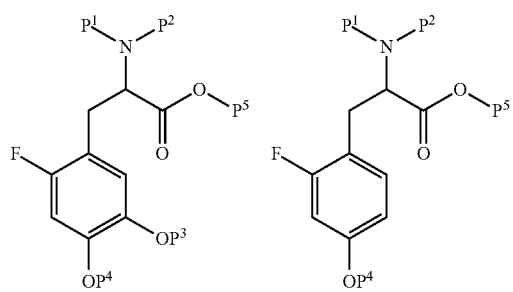

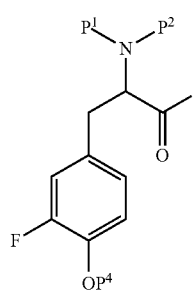

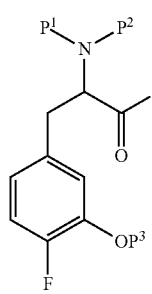 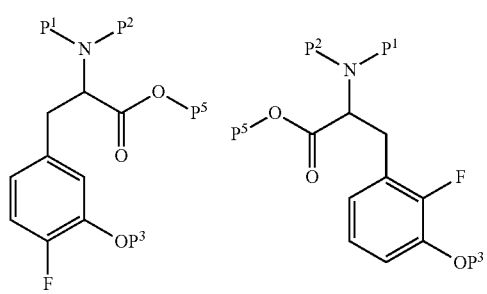

wherein each of P¹ and P² are independently a nitrogen protecting group, or P¹ and P² come together to form a single nitrogen protecting group; each of P³, and P⁴ are independently an alcohol protecting group, or P³ and P⁴ come together to form a single oxygen protecting group; and P⁵ is a carboxylic acid protecting group.

In some embodiments, the compound of Formula (1) or Formula (3) is chosen from:

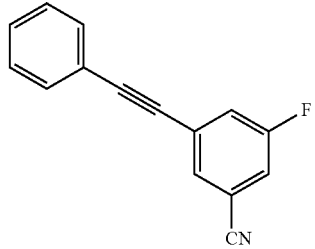

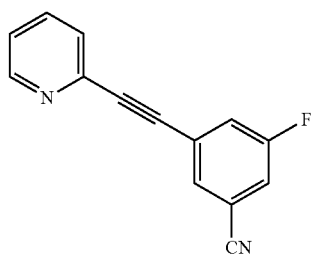

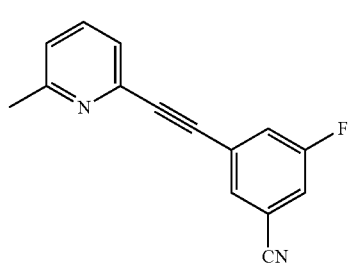

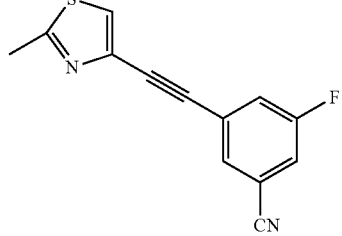

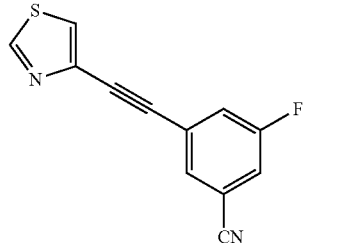

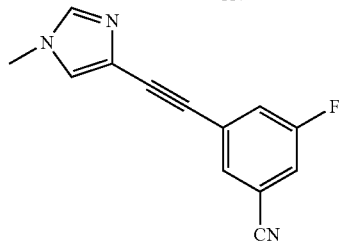

In some embodiments, the compound of Formula (1) or Formula (3) is chosen from:

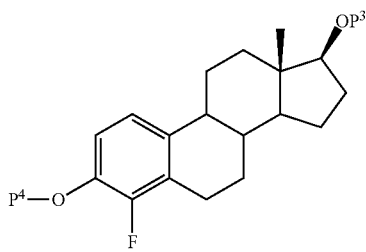

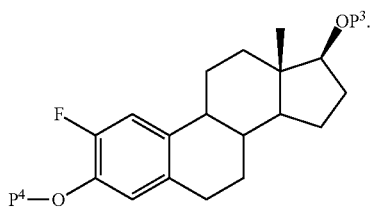

wherein each of $P^3$ and $P^4$ are independently an alcohol protecting group.

In some embodiments, the compound of Formula (1) or Formula (3) can be:

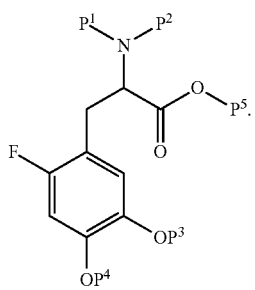

wherein each of $P^1$ and $P^2$ are independently a nitrogen protecting group, or $P^1$ and $P^2$ come together to form a single nitrogen protecting group; each of $P^3$, and $P^4$ are independently an alcohol protecting group, or $P^3$ and $P^4$ come together to form a single oxygen protecting group; and $P^5$ is a carboxylic acid protecting group. For example, the compound of Formula (1) or Formula (3) can be:

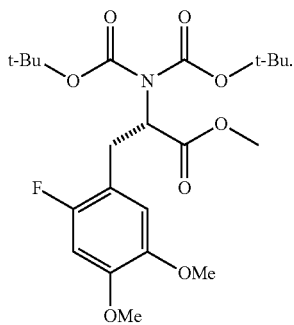

In some embodiments, the compound of Formula (1) or Formula (3) can be:

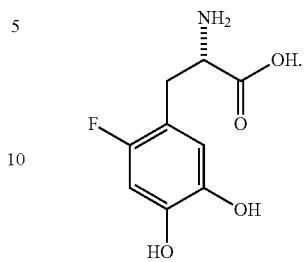

In some embodiments, the compound of Formula (7) can be:

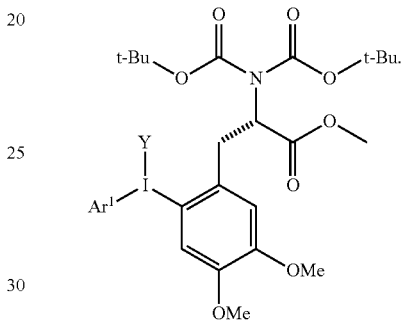

For example, the compound of Formula (7) can be:

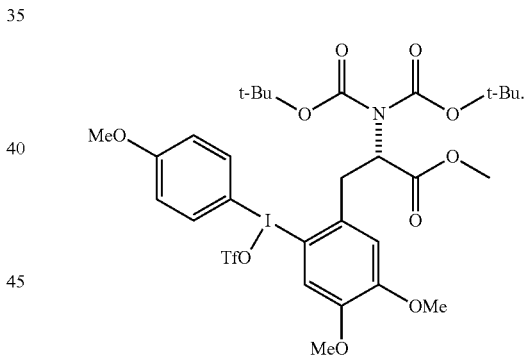

In some embodiments, the compound of Formula (6) can be:

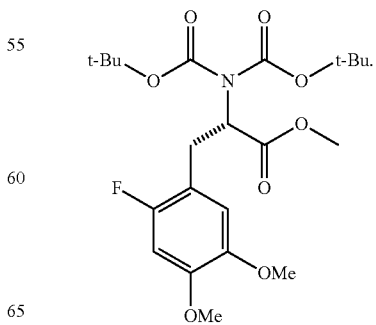

Also provided herein is a method for making a compound of Formula (1) that can include heating a mixture comprising a nonpolar solvent and a compound of Formula (5):

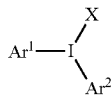

5 wherein Ar$^1$ is an electron rich aryl or heteroaryl ring system; and Ar$^2$ and X are as defined for Formula (1). In some embodiments, the reaction mixture is filtered (i.e., to remove insoluble material) prior to heating. In some embodiments, the reaction mixture is filtered and the nonpolar solvent is removed and the resulting residue is dissolved in a polar solvent prior to heating. In some embodiments, X is F (e.g., $^{18}$F).

Also provided herein is a method for making a compound of Formula (3) that can include heating a mixture comprising a nonpolar solvent and a compound of Formula (4):

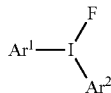

4 wherein Ar$^1$ is an electron rich aryl or heteroaryl ring system; and Ar$^2$ is as defined for Formula (3). In some embodiments, the reaction mixture is filtered (i.e., to remove insoluble material) prior to heating. In some embodiments, the reaction mixture is filtered and the nonpolar solvent is removed and the resulting residue is dissolved in a polar solvent prior to heating.

Further provided herein is a compound of Formula (8):

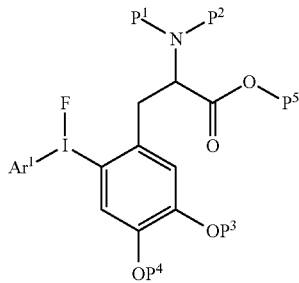

8 wherein Ar$^1$ is an electron rich aryl or heteroaryl ring system; each of P$^1$ and P$^2$ are independently a nitrogen protecting group, or P$^1$ and P$^2$ come together to form a single nitrogen protecting group; each of P$^3$ and P$^4$ are independently an alcohol protecting group, or P$^3$ and P$^4$ come together to form a single oxygen protecting group; and P$^5$ is a carboxylic acid protecting group. In some embodiments, the compound of Formula (8) is:

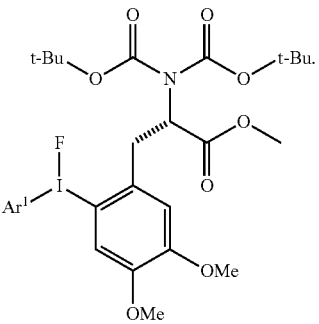

In some embodiments, the compound of Formula (8) is:

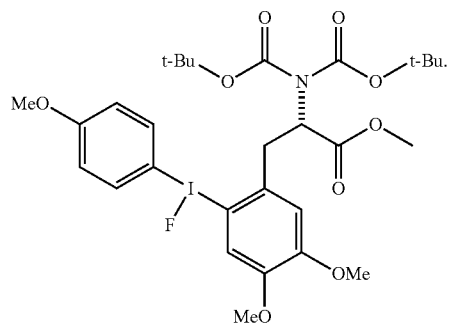

A compound of Formula (6) is also provided. The compound can be prepared using any of the methods described herein.

The details of one or more embodiments of the invention are set forth in the accompanying drawings and the description below. Other features, objects, and advantages of the invention will be apparent from the description and drawings, and from the claims.

DETAILED DESCRIPTION

Definitions

Figure 1:
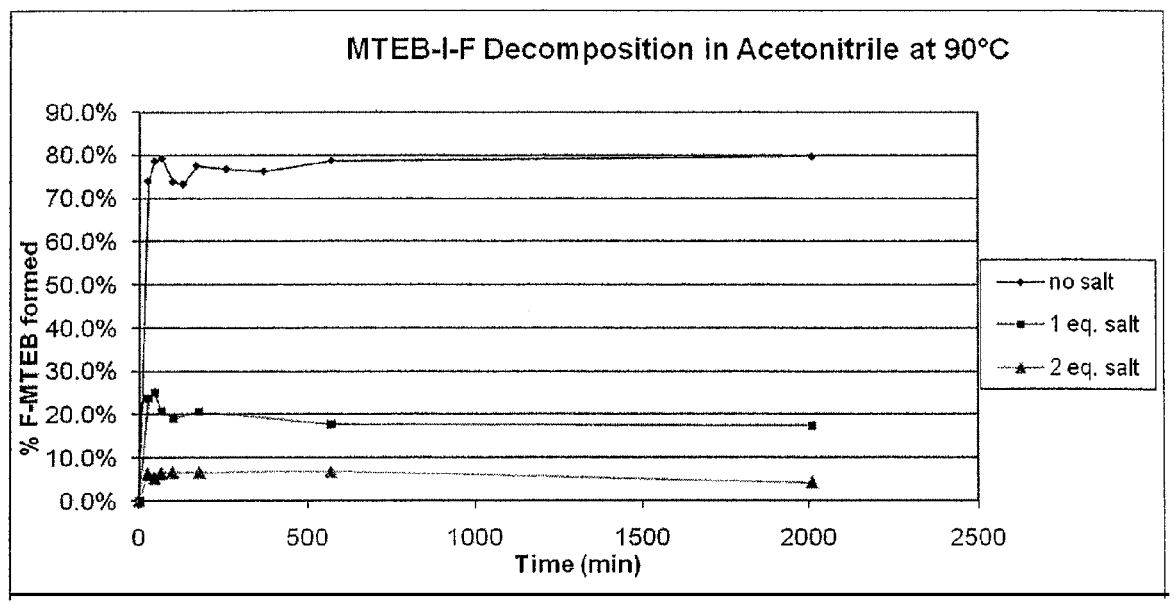
FIG. 1 shows the decomposition of MTEB-I-F in acetonitrile at 90° C.

Unless defined otherwise, all technical and scientific terms used herein have the same meaning as is commonly understood by one of ordinary skill in the art to which this disclosure belongs. All patents, applications, published applications, and other publications are incorporated by reference in their entirety. In the event that there is a plurality of definitions for a term herein, those in this section prevail unless stated otherwise.

As used herein, the singular forms "a," "an," and "the" include plural referents unless the context clearly dictates otherwise.

In general, the term "aryl" includes groups having 5 to 14 carbon atoms which form a ring structure and have an aromatic character, including 5- and 6-membered single-ring aromatic groups, such as benzene and phenyl. Furthermore, the term "aryl" includes polycyclic aryl groups, e.g., tricyclic, bicyclic, such as naphthalene and anthracene.

The term "heteroaryl" includes groups having 5 to 14 atoms which form a ring structure and have an aromatic character, including 5- and 6-membered single-ring aromatic groups, that have from one to four heteroatoms, for example, pyrrole, furan, thiophene, thiazole, isothiaozole, imidazole, triazole, tetrazole, pyrazole, oxazole isooxazole, pyridine, pyrazine, pyridazine, and pyrimidine, and the like. Furthermore, the term "heteroaryl" includes polycyclic heteroaryl groups, e.g., tricyclic, bicyclic, such as benzoxazole, benzodioxazole, benzothiazole, benzoimidazole, benzothiophene, methylenedioxyphenyl, quinoline, isoquinoline, napthridine, indole, benzofuran, purine, benzofuran, deazapurine, indazole, or indolizine.

The term "substituted" means that an atom or group of atoms formally replaces hydrogen as a "substituent" attached to another group. For aryl and heteroaryl groups, the term "substituted", unless otherwise indicated, refers to any level of substitution, namely mono, di, tri, tetra, or penta substitution, where such substitution is permitted. The substituents are independently selected, and substitution may be at any chemically accessible position.

The compounds provided herein may encompass various stereochemical forms and tautomers. The compounds also encompasses diastereomers as well as optical isomers, e.g. mixtures of enantiomers including racemic mixtures, as well as individual enantiomers and diastereomers, which arise as a consequence of structural asymmetry in certain compounds. Separation of the individual isomers or selective synthesis of the individual isomers is accomplished by application of various methods which are well known to practitioners in the art.

The term "electron rich", as used herein, refers to an aryl or heteroaryl ring system which is more easily oxidized than benzene. For example the aryl or heteroaryl ring system may be substituted with one or more substituents having a Hammett $\sigma_p$ value of less than zero.

The term "fluorine" unless explicitly stated otherwise includes all fluorine isotopes. Multiple fluorine isotopes are known, however, only $^{19}F$ is stable. The radioisotope $^{18}F$ has a half-life of 109.8 minutes and emits positrons during radioactive decay. The relative amount of $^{18}F$ present at a designated site in a compound of this disclosure will depend upon a number of factors including the isotopic purity of $^{18}F$ labeled reagents used to make the compound, the efficiency of incorporation of $^{18}F$ in the various synthesis steps used to prepare the compound, and the length of time since the $^{18}F$ has been produced. When a position is designated specifically as $^{18}F$ in the methods and compounds of the present disclosure, the position is understood to have at least about 0.01%, at least about 0.1%, at least about 1%, at least about 2%, at least about 3%, at least about 4%, at least about 5%, at least about 10%, at least about 15%, at least about 20%, at least about 25%, at least about 30%, at least about 35%, at least about 45%, at least about 50%, at least about 55%, at least about 60%, at least about 65%, at least about 70%, at least about 75%, at least about 80%, or at least about 85% $^{18}F$ incorporation at that site.

Methods of Preparing Substituted Aryl and Heteroaryl Ring Systems

Provided herein are methods of preparing substituted aryl and heteroaryl ring systems using diaryliodonium compounds and intermediates. For example, diaryliodonium salts and diaryliodonium fluorides, as provided herein, can undergo decomposition to prepare an aryl fluoride.

For example, provided herein is a method for making a compound of Formula (1):

    1 wherein $Ar^2$ is an aryl or heteroaryl ring system; and X is a moiety wherein the pKa of the acid H—X is less than 12. In some embodiments, a compound of Formula (1) can be prepared as shown in Scheme 1.

Scheme 1.

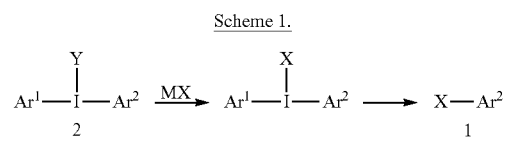

In some embodiments, the method can include reacting in a polar solvent a compound MX, wherein M is a counter ion and X is as defined in Formula (1), and a compound of Formula (2):

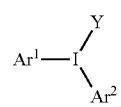    2 wherein $Ar^1$ is an electron rich aryl or heteroaryl ring system; Y is a leaving group; and $Ar^2$ and X are as defined above in Formula (1). The polar solvent can then be removed from the reaction mixture. The remaining mixture can then be combined with a nonpolar solvent and heated to produce a compound of Formula (1).

In some embodiments, the method can include heating a mixture comprising a nonpolar solvent, a compound MX, and a compound of Formula (2).

In some embodiments, the nonpolar solution of the reaction mixture of MX and a compound of Formula (2) can be filtered prior to heating. The filtration step can remove any insoluble material (e.g., insoluble salts) that remain in the reaction mixture. In some embodiments, the solvent can be removed from the filtrate prior to heating (i.e., the residue can be heated neat).

In further embodiments, the nonpolar solution of the reaction mixture of MX and a compound of Formula (2) can be filtered prior to heating, the nonpolar solvent can be removed (e.g., by evaporation), and the heating of the sample can be performed in a different solvent.

Substituted aryls and heteroaryls which are prepared using the methods described herein can have an X moiety which includes any moiety in which the pKa of H—X (i.e., the conjugate acid of X) is less than about 12. In some cases, X is a radioactive isotope (e.g., $^{18}F$, $^{123}I$, $^{131}I$, and compounds having $^{32}P$ and $^{33}P$). In some embodiments, X can be chosen from halide, aryl carboxylate, alkyl carboxylate, phosphate, phosphonate, phosphonite, azide, thiocyanate, cyanate, phenoxide, triflate, trifluoroethoxide, thiolates, and stabilized enolates. For example, X can be fluoride, chloride, bromide, iodide, trifluoroacetate, benzoate, and acetate. In some embodiments, X is fluoride. In some embodiments, is a radioactive isotope of fluoride (e.g., $^{18}F$).

Y can be any suitable leaving group. In some embodiments, Y is a weakly coordinating anion (i.e., an anion that coordinates only weakly with iodine). For example, Y can be the conjugate base of a strong acid, for example, any anion for which the pKa of the conjugate acid (H—Y) is less than about 1. For example, Y can be triflate, mesylate, nonaflate, hexaflate, toluene sulfonate (tosylate), nitrophenyl sulfonate (nosylate), bromophenyl sulfonate (brosylate), perfluoroalkyl sulfonate (e.g., perfluoro $C_{2-10}$ alkyl sulfonate), tetraphenylborate, hexafluorophosphate, trifluoroacetate, perfluoroalkylcarboxylate, tetrafluoroborate, perchlorate, hexafluorostibate, hexachlorostibate, chloride, bromide, or iodide. In some embodiments, a slightly more basic leaving group such as acetate or benzoate may be used.

The counter ion M can be any suitable cation for the desired X. The choice of the source of X, and accordingly M, is readily within the knowledge of one of ordinary skill in the art. For example, M can be chosen from an alkali metal, alkaline earth metal and transition metal salts such as, for example, calcium, magnesium, potassium, sodium and zinc salts. Metal cations may also be complexed to cryptands or crown ethers to enhance their solubility and to labilize the X moiety. M can also include organic salts made from quaternized amines derived from, for example, N,N' dibenzylethylenediamine, chloroprocaine, choline, diethanolamine, ethylenediamine, meglumine (N-methylglucamine) and procaine. In some embodiments, M can be a lithium, sodium, potassium, or cesium with cryptands or crown ethers, a tetrasubstituted ammonium cation, or phosphonium cation. When X is fluoride, the choice of fluoride source is also readily within the knowledge of one of ordinary skill in the art. A variety of fluoride sources can be used in the preparation of the fluorinated aryl and heteroaryl compounds as provided herein, including but not limited to NaF, KF, CsF, tetrabutylammonium fluoride, and tetramethylammonium fluoride. In certain instances the choice of fluoride source will depend on the functionality present on the compound of Formula (2).

The methods described above can be useful in the preparation of fluorinated aryl and heteroaryl ring systems. For example, the methods can be used to prepare a compound of Formula (3):

$$Ar^2—F \qquad 3$$

wherein $Ar^2$ is an aryl or heteroaryl ring system. In particular, the methods can be used to prepare radiolabeled fluorinated aryl and heteroaryl ring systems (e.g., PET radiotracers). In some embodiments, the method can include reacting in a polar solvent a compound MF and a compound of Formula (2). The polar solvent can then be removed from the reaction mixture. The remaining mixture can then be combined with a nonpolar solvent and heated to produce a compound of Formula (3).

In some embodiments, the method can include heating a mixture comprising a nonpolar solvent, a compound MF, and a compound of Formula (2).

In some embodiments, the nonpolar solution of the reaction mixture of MF and a compound of Formula (2) can be filtered prior to heating. The filtration step can remove any insoluble material (e.g., insoluble salts) that remain in the reaction mixture. In some embodiments, the solvent can be removed from the filtrate prior to heating (i.e., the residue can be heated neat).

In some embodiments, the nonpolar solution of the reaction mixture of MF and a compound of Formula (2) can be filtered prior to heating, the nonpolar solvent can be removed (e.g., by evaporation), and the heating of the sample can be performed in a different solvent.

In some embodiments, the compound of Formula (3) can be a compound of Formula (6):

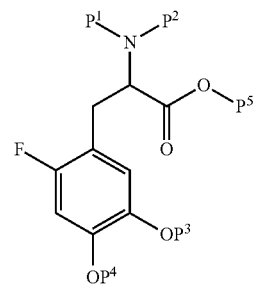

6 wherein each of $P^1$ and $P^2$ are independently a nitrogen protecting group, or $P^1$ and $P^2$ come together to form a single nitrogen protecting group; each of $P^3$, and $P^4$ are independently an alcohol protecting group, or $P^3$ and $P^4$ come together to form a single oxygen protecting group; and $P^5$ is a carboxylic acid protecting group. In some embodiments, the method can include reacting in a polar solvent a compound MF and a compound of Formula (7):

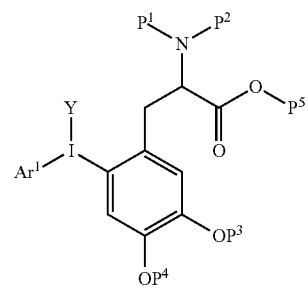

7 wherein $Ar^1$ is an electron rich aryl or heteroaryl ring system; Y is a leaving group; and $P^1$, $P^2$, $P^3$, $P^4$ and $P^5$ are as defined in Formula (6). The polar solvent can then be removed from the reaction mixture. The remaining mixture can then be combined with a nonpolar solvent and heated to produce a compound of Formula (6).

In some embodiments, the method can include heating a mixture comprising a nonpolar solvent, a compound MF, and a compound of Formula (7).

In some embodiments, the nonpolar solution of the reaction mixture of MF and a compound of Formula (7) can be filtered prior to heating. The filtration step can remove any insoluble material (e.g., insoluble salts) that remain in the reaction mixture. In some embodiments, the solvent can be removed from the filtrate prior to heating (i.e., the residue can be heated neat).

The compound of Formula (6) can be, for example,

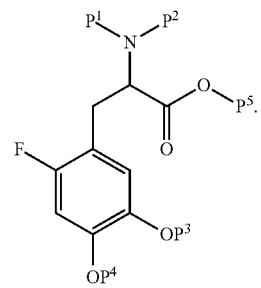

In some embodiments, the compound of Formula (6) is:

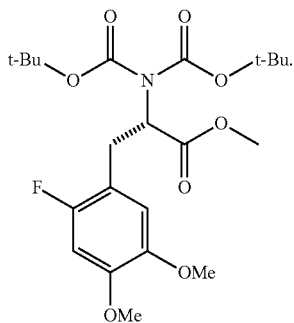

Accordingly, the compound of Formula (7) can be, for example:

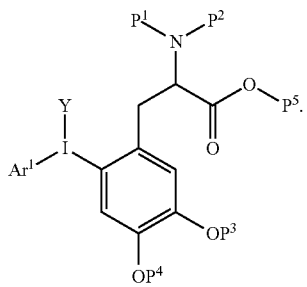

In some embodiments, the compound of Formula (7) can be:

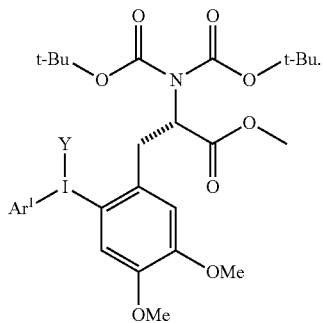

In some embodiments, the compound of Formula (7) can be:

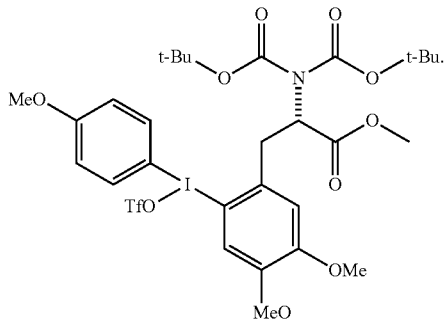 [SMILES: COC(=O)[C@H](Cc1cc(OC)c(OC)cc1I(OS(=O)(=O)C(F)(F)F)c1ccc(OC)cc1)N(C(=O)OC(C)(C)C)C(=O)OC(C)(C)C]

The moiety $Ar^1$ can be an electron-rich aryl or heteroaryl ring system. For example, in some embodiments, $Ar^1$—H is more easily oxidized than benzene. In some embodiments, $Ar^1$ can be substituted with at least one substituent having a Hammett $\sigma_p$ value of less than zero (see, for example, "A survey of Hammett substituent constants and resonance and field parameters", Corwin. Hansch, A. Leo, R. W. Taft *Chem. Rev.*, 1991, 91 (2), pp 165-195). For example, $Ar^1$ can be substituted with at least one of —$(C_1-C_{10})$alkyl, —$(C_1-C_{10})$haloalkyl, $(C_2-C_{10})$alkenyl, $(C_2-C_{10})$alkynyl, —O—$(C_1-C_{10})$alkyl, —C(O)—O—$(C_1-C_{10})$alkyl, aryl, and heteroaryl. In some embodiments, $Ar^1$ is:

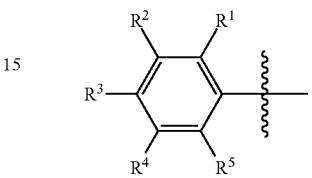

wherein $R^1$, $R^2$, $R^3$, $R^4$, and $R^5$ are independently chosen from: H, —$(C_1-C_{10})$alkyl, —$(C_1-C_{10})$haloalkyl, $(C_2-C_{10})$alkenyl, $(C_2-C_{10})$alkynyl, —O—$(C_1-C_{10})$alkyl, —C(O)—O—$(C_1-C_{10})$alkyl, aryl, and heteroaryl, or two or more of $R^1$, $R^2$, $R^3$, $R^4$, and $R^5$ come together to form a fused aryl or heteroaryl ring system.

In some embodiments, $Ar^1$ is the same as $Ar^2$. In some embodiments, $Ar^1$ is more easily oxidized than $Ar^2$.

In some embodiments, $Ar^1$ can be substituted with a solid support. A "solid support" may be any suitable solid-phase support which is insoluble in any solvents to be used in the process but which can be covalently bound (e.g., to $Ar^1$ or to an optional linker). Examples of suitable solid supports include polymers such as polystyrene (which may be block grafted, for example with polyethylene glycol), polyacrylamide, or polypropylene or glass or silicon coated with such a polymer. The solid support may be in the form of small discrete particles such as beads or pins, or as a coating on the inner surface of a reaction vessel, for example a cartridge or a microfabricated vessel. See, for example, U.S. Patent Application No. 2007/0092441.

In some embodiments, the solid support is covalently bound to $Ar^1$ through the use of a linker. A "linker" can be any suitable organic group which serves to space the $Ar^1$ from the solid support structure so as to maximize reactivity. For example, a linker can include a $C_{1-20}$ alkyl or a $C_{1-20}$ alkoxy, attached to the solid support, for example, a resin by an amide ether or a sulphonamide bond for ease of synthesis. The linker may also be a polyethylene glycol (PEG) linker. Examples of such linkers are well known to those skilled in the art of solid-phase chemistry.

The methods described herein can be used with a variety of aryl and heteroaryl ring systems. As is well understood by one of skill in the art, to carry out efficient nucleophilic substitution of the aryl and heteroaryl ring systems described herein, it is necessary that $Ar^1$ be more easily oxidized (i.e., more electron rich) than $Ar^2$. Within that boundary, however, the $Ar^2$ moiety can be any aryl or heteroaryl ring system in which substitution by X (e.g., F such as $^{18}$F) is desired. For example, $Ar^2$ can be a phenylalanine, tyrosine, typtophan, or histidine derivative, and an estradiol derivative. In some embodiments, $Ar^2$ can be chosen from:

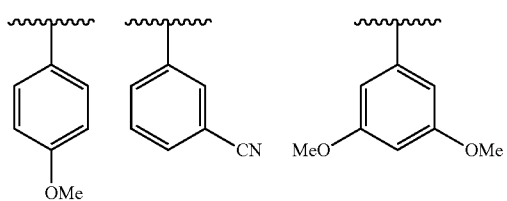
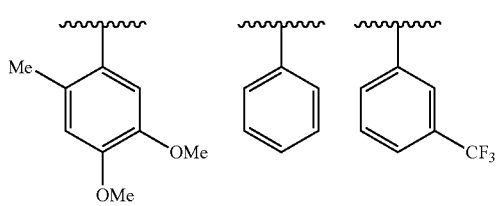
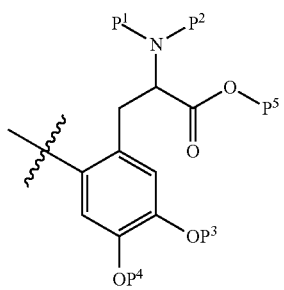
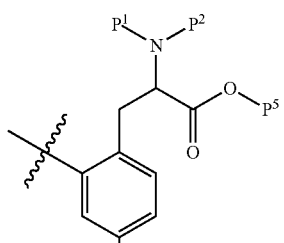
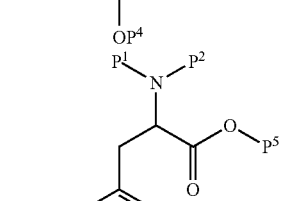
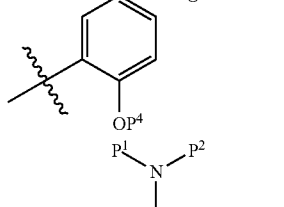
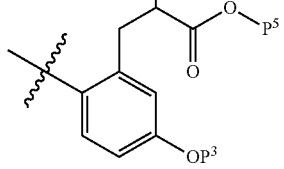
-continued
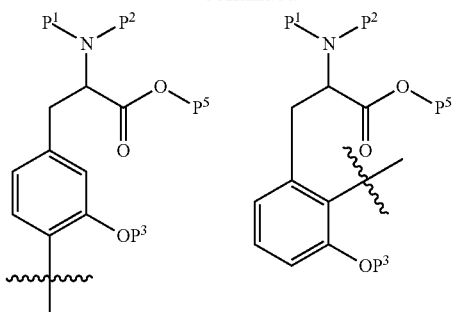
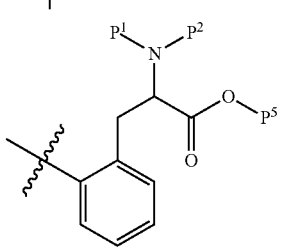
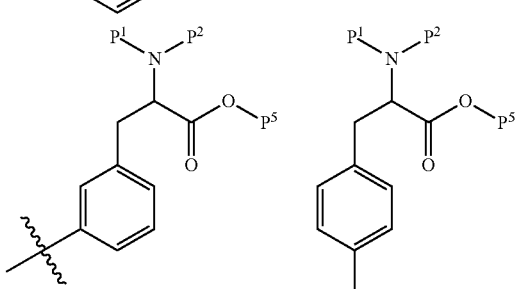
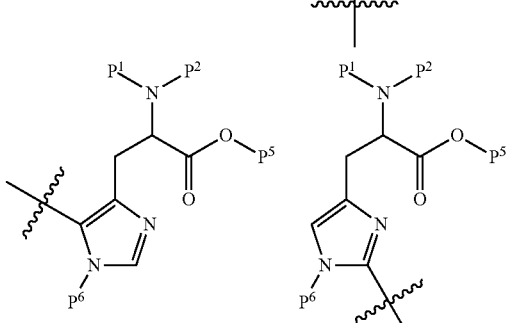
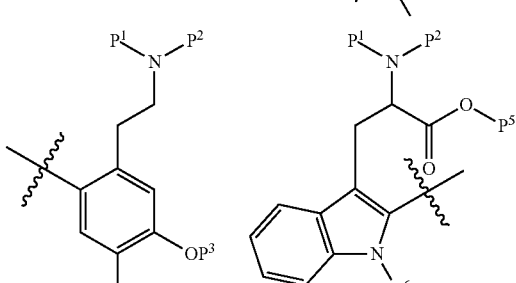
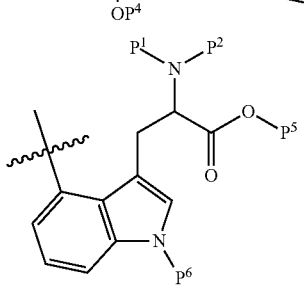

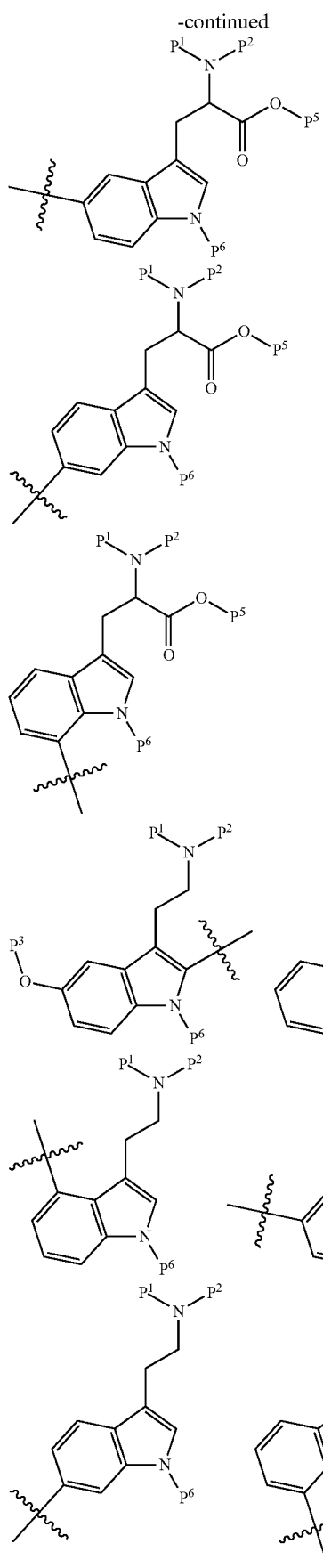
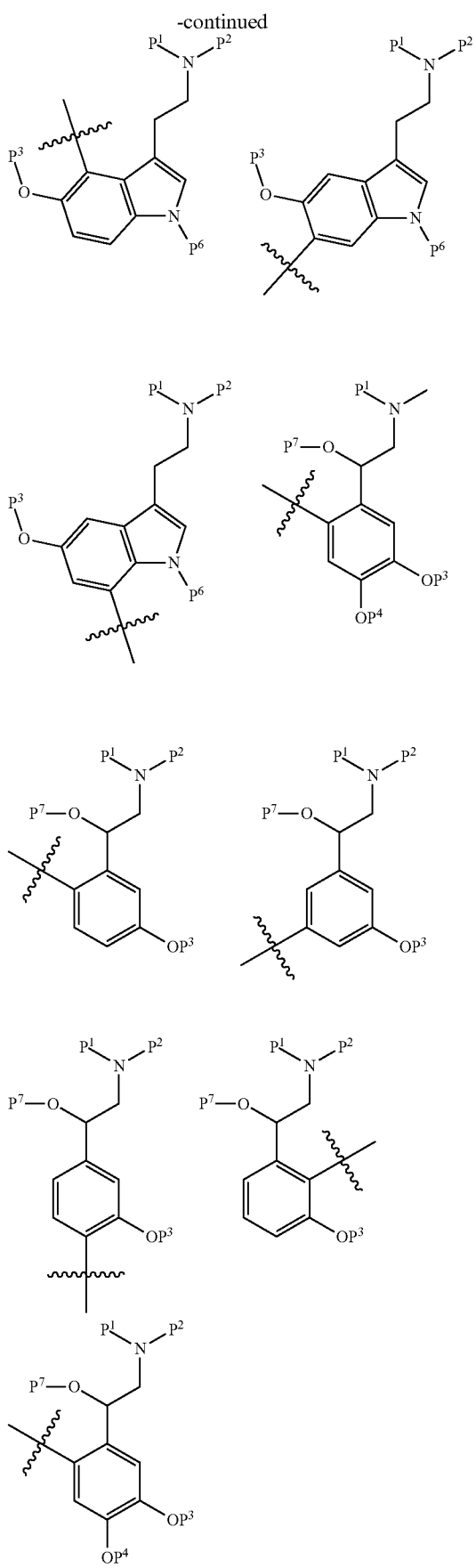

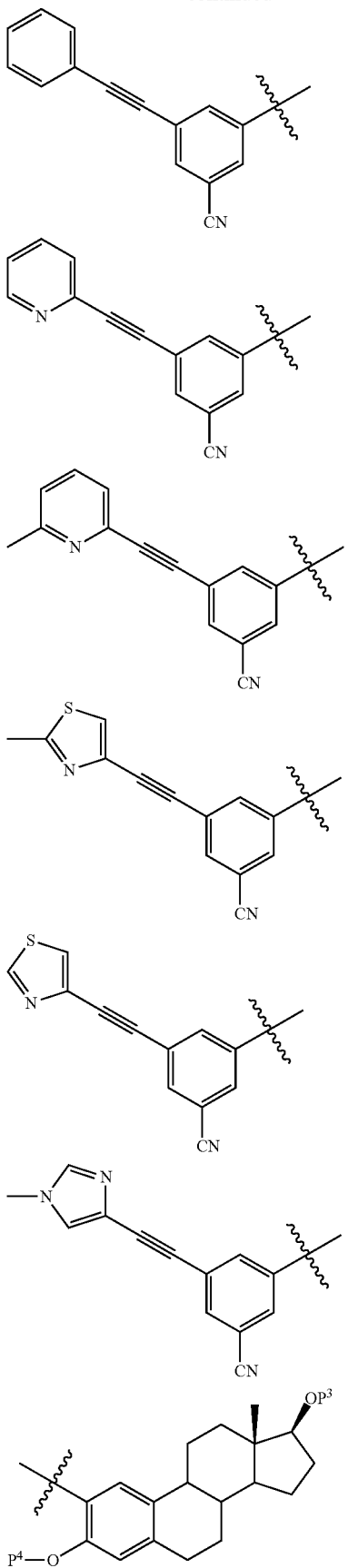

wherein each of $P^1$, $P^2$ and $P^6$ are independently a nitrogen protecting group, or $P^1$ and $P^2$ come together to form a single nitrogen protecting group; and each of $P^3$, $P^4$, $P^5$ and $P^7$ are independently an oxygen protecting group, or $P^3$ and $P^4$ come together to form a single oxygen protecting group. In some embodiments, $Ar^2$ is an electron rich aryl or heteroaryl ring system.

Protecting groups can be a temporary substituent which protects a potentially reactive functional group from undesired chemical transformations. The choice of the particular protecting group employed is well within the skill of one of ordinary skill in the art. A number of considerations can determine the choice of protecting group including, but not limited to, the functional group being protected, other functionality present in the molecule, reaction conditions at each step of the synthetic sequence, other protecting groups present in the molecule, functional group tolerance to conditions required to remove the protecting group, and reaction conditions for the thermal decomposition of the compounds provided herein. The field of protecting group chemistry has been reviewed (Greene, T. W.; Wuts, P. G. M. *Protective Groups in Organic Synthesis,* 2.sup.nd ed.; Wiley: New York, 1991).

A nitrogen protecting group can be any temporary substituent which protects an amine moiety from undesired chemical transformations. Examples of such protecting groups include, but are not limited to allylamine, benzylamines (e.g., bezylamine, p-methoxybenzylamine, 2,4-dimethoxybenzylamine, and tritylamine), acetylamide, trichloroacetammide, trifluoroacetamide, pent-4-enamide, phthalimides, carbamates (e.g., methyl carbamate, t-butyl carbamate, benzyl carbamate, allyl carbamates, 2,2,2-trichloroethyl carbamate, and 9-fluorenylmethyl carbamate), imines, and sulfonamides (e.g., benzene sulfonamide, p-toluenesulfonamide, and p-nitrobenzenesulfonamide).

An oxygen protecting group can be any temporary substituent which protects a hydroxyl moiety from undesired chemical transformations. Examples of such protecting groups include, but are not limited to esters (e.g., acetyl, t-butyl carbonyl, and benzoyl), benzyl (e.g., benzyl, p-methoxybenzyl, and 2,4-dimethoxybenzyl, and trityl), carbonates (e.g., methyl carbonate, allyl carbonate, 2,2,2-trichloroethyl carbonate and benzyl carbonate) ketals, and acetals, and ethers.

In some embodiments, a compound of Formula (2), as provided herein, can be chosen from:

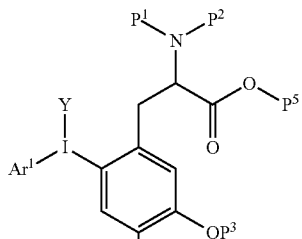

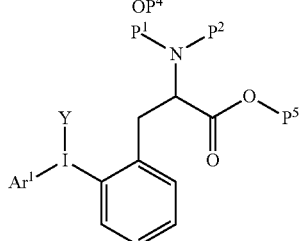

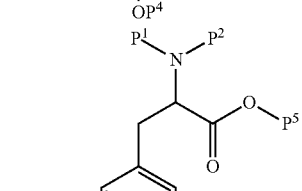

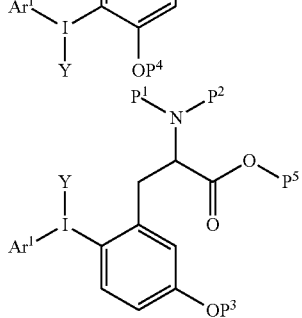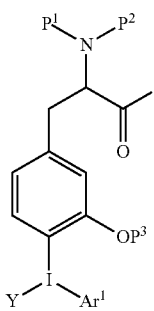

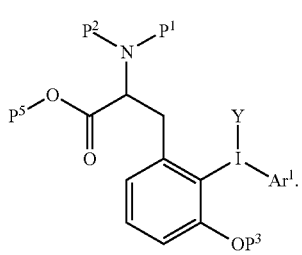

wherein:
each of $P^1$ and $P^2$ are independently a nitrogen protecting group, or $P^1$ and $P^2$ come together to form a single nitrogen protecting group;
each of $P^3$ and $P^4$ are independently an oxygen protecting group, or $P^3$ and $P^4$ come together to form a single oxygen protecting group, and $P^5$ is a carboxylic acid protecting group. For example, a compound of Formula (2) can be:

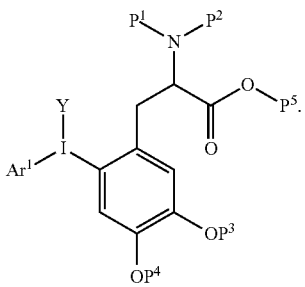

In some embodiments, a compound of Formula (2) can be:

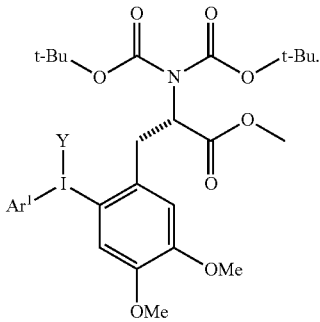

In some embodiments, a compound of Formula (2) can be:

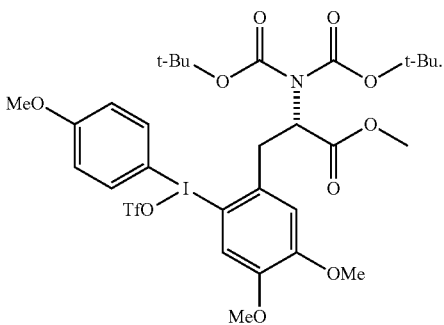 [SMILES: COC(=O)[C@H](Cc1cc(OC)c(OC)cc1I(OS(=O)(=O)C(F)(F)F)c1ccc(OC)cc1)N(C(=O)OC(C)(C)C)C(=O)OC(C)(C)C]

In some embodiments, a compound of Formula (2) is chosen from:

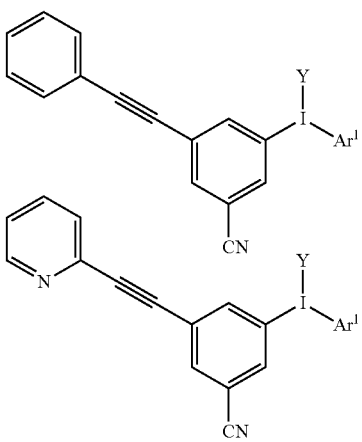

-continued

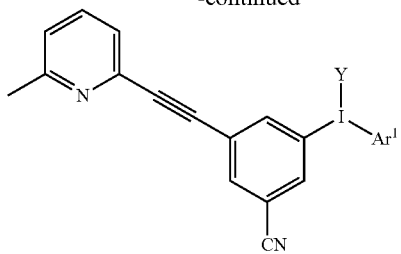

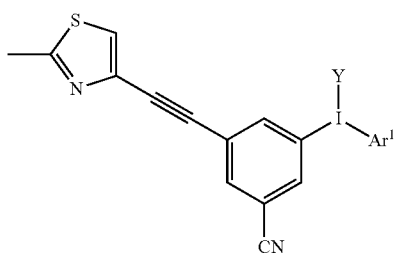

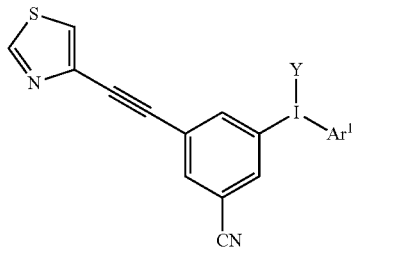

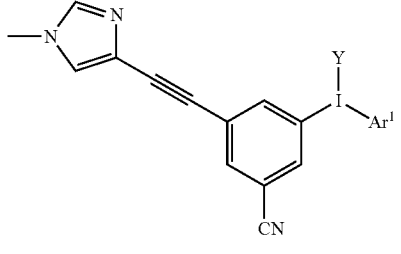

In other embodiments, a compound of Formula (2) is chosen from:

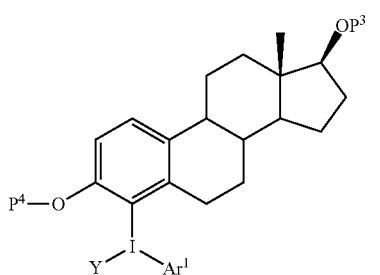

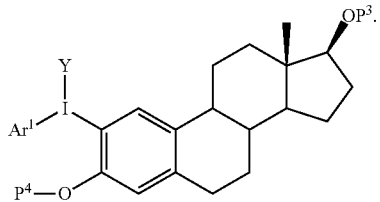

wherein:
each of $P^3$ and $P^4$ are independently an alcohol protecting group.

In some embodiments, a compound of Formula (1) or Formula (3) can be chosen from:

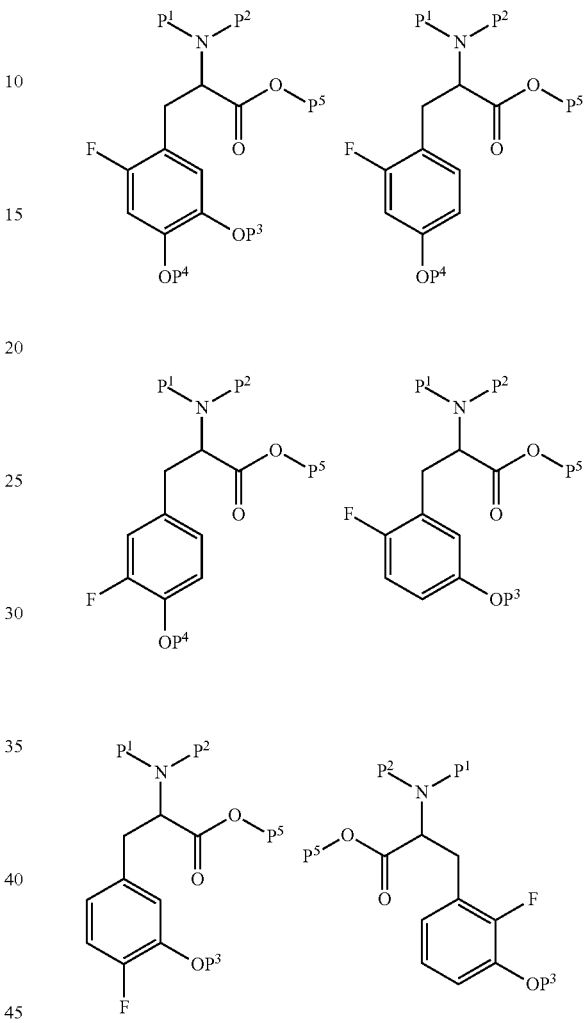

wherein each of $P^1$ and $P^2$ are independently a nitrogen protecting group, or $P^1$ and $P^2$ come together to form a single nitrogen protecting group; and each of $P^3$ and $P^4$ are independently an alcohol protecting group, or $P^3$ and $P^4$ come together to form a single oxygen protecting group, and $P^5$ is a carboxylic acid protecting group. For examples, a compound of Formula (1) or Formula (3) can be:

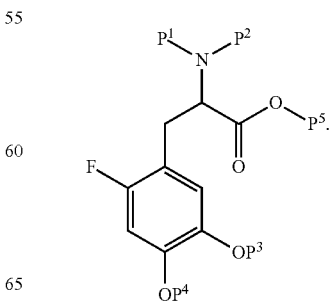

In some embodiments, a compound of Formula (1) or Formula (3) can be:

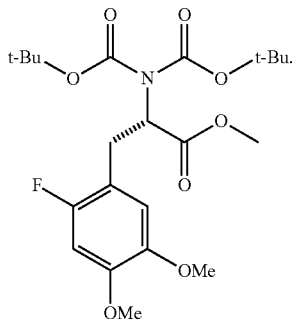

In some embodiments, a compound of Formula (1) or Formula (3) can be:

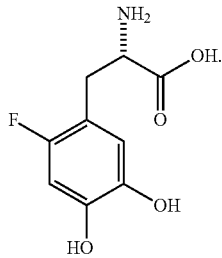 [SMILES: N[C@@H](Cc1cc(O)c(O)cc1F)C(=O)O]

In some embodiments, a compound of Formula (1) or Formula (3) can be chosen from:

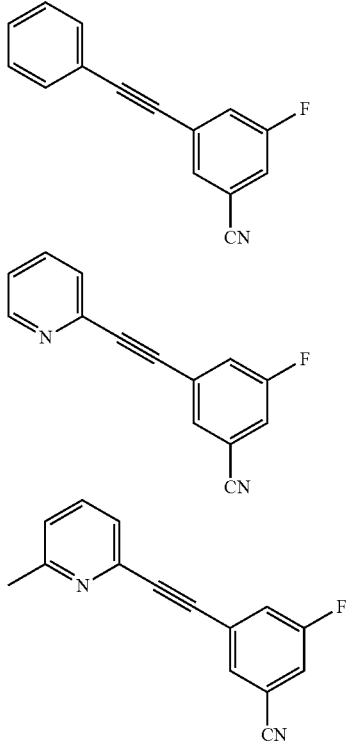

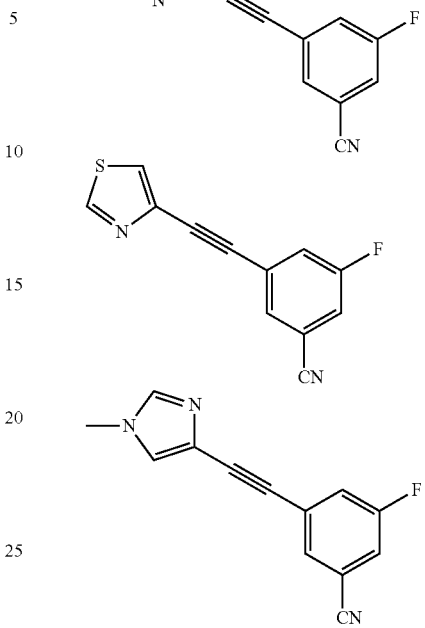

In some embodiments, a compound of Formula (1) or Formula (3) is chosen from:

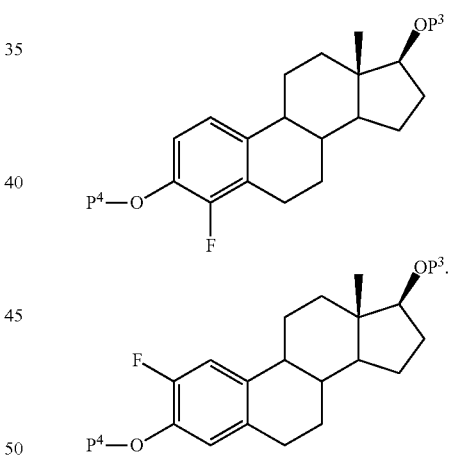

wherein each of $P^3$ and $P^4$ are independently an alcohol protecting group.

A nonpolar solvent can be any solvent having a dielectric constant of less than about 10. For example, a nonpolar solvent can be chosen from benzene, toluene, o-xylene, m-xylene, p-xylene, ethyl benzene, carbon tetrachloride, hexane, cyclohexane, fluorobenzene, chlorobenzene, nitrobenzene, and mixtures thereof. In some embodiments, the nonpolar solvent comprises benzene. In some embodiments, the nonpolar solvent comprises toluene. In some embodiments, the nonpolar solvent comprises cyclohexane. In some embodiments the nonpolar solvent is a mixture, for example a mixture of cyclohexane and toluene.

A polar solvent is a solvent having a dielectric constant greater than about 10. In some embodiments, the polar solvent is a polar aprotic solvent, such as acetonitrile, acetone, dichloromethane, ethyl acetate, tetrahydrofuran, dimethylformamide, 1,2-difluorobenzene, benzotrifluoride, and mixtures thereof. In some embodiments, the polar aprotic solvent is acetonitrile.

Heating can be accomplished by conventional means (e.g., heating bath, oven, heat gun, hot plate, Bunsen burner, heating mantle, and the like), by the use of a microwave, or by flash pyrolysis. Typically, the reaction mixture is heated at a temperature ranging from about 25° C. to about 250° C. (e.g., between about 80° C. to about 200° C., 100° C. to about 200° C., about 120° C. to about 170° C., about 120° C. to about 160° C., about 120° C. to about 150° C., and about 130° C. to about 150° C.). In some embodiments, the reaction mixture is heated to about 140° C. Heating can occur for any time necessary to complete the reaction. For example, heating can occur for from about 1 second to about 25 minutes (e.g., about 2 seconds, about 5 seconds, about 10 seconds, about 30 seconds, about 1 minute, about 90 seconds, about 2 minutes, about 3 minutes, about 5 minutes, about 8 minutes, about 10 minutes, about 12 minutes, about 15 minutes, about 20 minutes, and about 24 minutes). In some embodiments, heating can occur for from about 1 second to about 15 minutes.

Further provided herein is a method of making a compound of Formula (1) that includes heating a mixture comprising a nonpolar solvent and a compound of Formula (5):

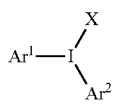

5 wherein $Ar^1$ is an electron rich aryl or heteroaryl ring system; and $Ar^2$ and X are as defined for Formula (1). In some embodiments, the method can include filtering the mixture prior to heating. Filtering, as described above, can remove insoluble materials such as insoluble salts. In another embodiment, the method can include, prior to heating, filtering the mixture, removing the nonpolar solvent, and subsequently heating a solution of the remaining reaction mixture and a polar solvent.

As described above, the methods described herein can be used to prepare fluorinated (e.g., $^{18}F$) aryl and heteroaryl ring systems. Accordingly, further provided herein is a method for making a compound of Formula (3) that includes heating a mixture comprising a nonpolar solvent and a compound of Formula (4):

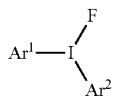

4 wherein $Ar^1$ is an electron rich aryl or heteroaryl ring system; and $Ar^2$ is as defined for Formula (3). In some embodiments, the method can include filtering the mixture prior to heating. Filtering, as described above, can remove insoluble materials such as insoluble salts. In another embodiment, the method can include, prior to heating, filtering the mixture, removing the nonpolar solvent, and subsequently heating a solution of the remaining reaction mixture and a polar solvent.

In the methods described herein, a pressure tube or other reinforced closed system can be used in instances where the desired temperature is above the boiling point of the solvent utilized.

The reaction can be conducted in the presence of an inert gas such as nitrogen or argon. In some embodiments, steps are taken to remove oxygen and/or water from the reaction solvent and starting materials. This can be accomplished by a number of methods including distillation of solvents in the presence of agents that react with and/or sequester water and under an atmosphere of inert gas; and purging the reaction vessel with an inert gas.

The methods described herein can be used when MX (e.g., MF) is reacted in an amount ranging from about 1 picomole to about 10 millimoles (e.g., about 1 picomole to about 5 millimoles; about 1 picomole to about 1 millimole; about 1 picomole to about 500 micromoles; about 1 picomole to about 100 micromoles; about 1 picomole to about 50 micromoles; about 1 picomole to about 5 micromoles; about 1 picomole to about 1 micromole; about 1 picomole to about 500 nanomoles; about 1 picomole to about 100 nanomoles; about 1 picomole to about 50 nanomoles; about 1 picomole to about 5 nanomoles; about 1 picomole to about 1 nanomole; about 100 picomoles to about 10 millimoles; about 500 picomoles to about 10 millimoles; about 1 nanomole to about 10 millimoles; about 50 nanomoles to about 10 millimoles; about 100 nanomoles to about 10 millimoles; about 500 nanomoles to about 10 millimoles; about 1 micromole to about 10 millimoles; about 50 micromoles to about 10 millimoles; about 100 micromoles to about 10 millimoles; about 500 micromoles to about 10 millimoles and about 1 millimole to about 10 millimoles). In some embodiments, MX is reacted in the sample in an amount of less than about 10 millimoles. In many cases, the compound of Formula (2) is used in an excess when compared to the amount of MX present in the sample. In some embodiments, the reaction mixture having MX further contains additional compounds which may be present in an excess compared to MX. For example, the additional compounds may be present in more than one million fold excess compared to MX.

Compounds

Diaryliodonium compounds, for example, compound of Formula (2), (4), (7) and (8), are further provided herein. For example, a compound of Formula (8) is provided,

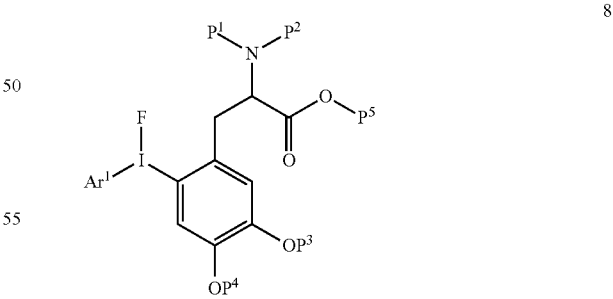

8 wherein $Ar^1$ is an electron rich aryl or heteroaryl ring system; each of $P^1$ and $P^2$ are independently a nitrogen protecting group, or $P^1$ and $P^2$ come together to form a single nitrogen protecting group; each of $P^3$, and $P^4$ are independently an alcohol protecting group, or $P^3$ and $P^4$ come together to form a single oxygen protecting group; and $P^5$ is a carboxylic acid protecting group. In some embodiments, the compound of Formula (8) can be:

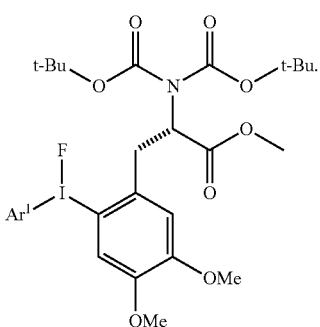

In some embodiments, a compound of Formula (8) can be:

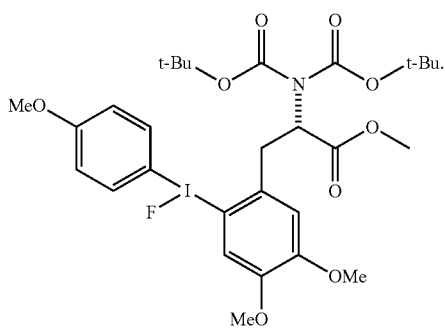 [SMILES: COC(=O)[C@H](Cc1cc(OC)c(OC)cc1I(F)c1ccc(OC)cc1)N(C(=O)OC(C)(C)C)C(=O)OC(C)(C)C]

The diaryliodonium compounds of Formula (2), (4) and (7) can be prepared from commercially available starting materials using various methods known to those of ordinary skill in the art. The method used for synthesizing the compounds will depend on the electronics and functionality present in of $Ar^2$. Potentially reactive functional groups present in $Ar^2$ can be masked using a protecting group prior to the synthesis of the diaryliodonium compound. The particular method employed for preparing the diaryliodonium compounds will be readily apparent to a person of ordinary skill in the art. For example, the compounds can be made using the following generic reactions as shown in Scheme 2.

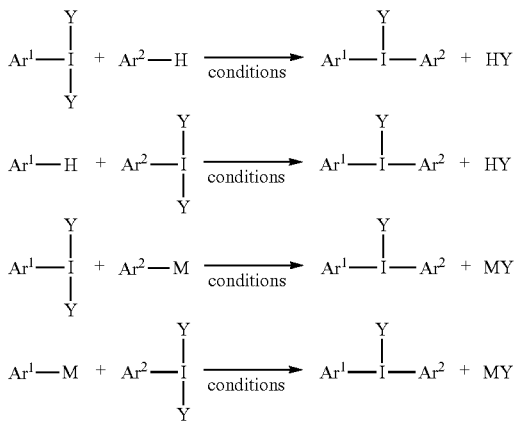

For compounds that bear sensitive functionality on the accepting group, organometallic reagents that feature more covalent (more stable) C-M bonds can be used. For example, organometallic compounds including tin, boron, and zinc. If there is no functional group incompatibility, more basic organometallic reagents (organolithium, Grignard, etc.) can be used to prepare the diaryliodonium salts.

Persons skilled in the art will be aware of variations of, and alternatives to, the processes described which allow the compounds defined herein to be obtained.

It will also be appreciated by persons skilled in the art that, within certain of the processes described, the order of the synthetic steps employed may be varied and will depend inter alia on factors such as the nature of other functional groups present in a particular substrate, the availability of key intermediates, and the protecting group strategy (if any) to be adopted. Clearly, such factors will also influence the choice of reagent for use in the said synthetic steps.

The skilled person will appreciate that the diaryliodonium compounds described could be made by methods other than those herein described, by adaptation of the methods herein described and/or adaptation of methods known in the art, for example US 2007/0092441, or using standard textbooks such as "Comprehensive Organic Transformations—A Guide to Functional Group Transformations", R C Larock, Wiley-VCH (1999 or later editions) and Science of Synthesis, Volume 31a, 2007 (Houben-Weyl, Thieme)

It is to be understood that the synthetic transformation methods mentioned herein are exemplary only and they may be carried out in various different sequences in order that the desired compounds can be efficiently assembled. The skilled chemist will exercise his judgment and skill as to the most efficient sequence of reactions for synthesis of a given target compound.

As exemplified in the examples below, certain diaryliodonium fluorides can be prepared by $H_2SO_4$ catalyzed electrophilic aromatic substitution of the aromatic fluorine precursor with $ArI(OAc)_2$, followed by ion exchange. The desired diaryliodonium fluoride is formed by reacting the resulting diaryliodonium salt with a fluoride source, such as tetrabutylammonium fluoride, as illustrated in Scheme 3 shown below.

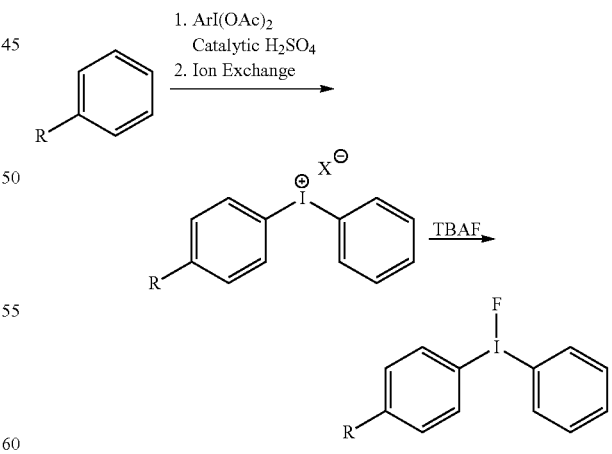

Diaryliodonium fluorides can also be prepared by the reaction of the corresponding tributylstannanyl derivative of the aromatic fluorine precursor with p-MeOPhI(OH)(OTs), followed by ion exchange, and reaction of the resulting diaryliodonium salt with a fluoride source, such as tetrabutylammonium fluoride, as illustrated in Scheme 4.

41

Scheme 4.

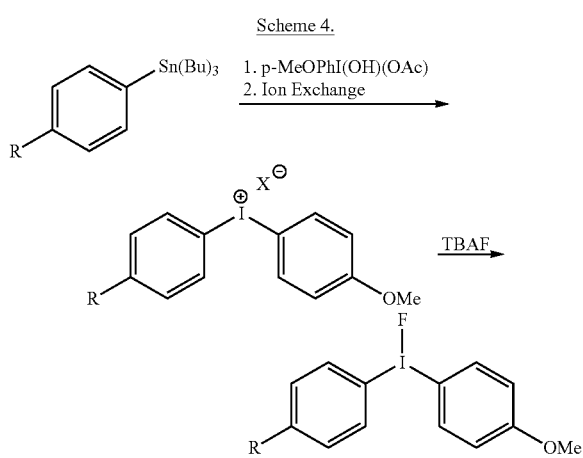

The choice of fluoride source is readily within the knowledge of one of ordinary skill in the art. A variety of fluoride sources can be used in the preparation of the diaryliodonium fluorides as provided herein, including but not limited to NaF, KF, CsF, tetrabutylammonium fluoride, and tetramethylammonium fluoride. In certain instances the choice of fluoride source will depend on the functionality present on the aromatic fluoride precursor.

Further provided are compounds of Formula (1) and Formula (3) which are prepared by the methods described herein. For example, a compound of Formula (6) is provided, wherein the compound is prepared as described above.

EXAMPLES

General Methods

Tetramethylammonium fluoride (TMAF, Aldrich) and diphenyliodonium nitrate were dried at 60-80° C. in a drying pistol (charged with $P_2O_5$) under dynamic vacuum for one week. Hexabutylditin and tributyltin chloride (Aldrich) were distilled into flame-dried storage tubes under dry nitrogen. Acetonitrile and acetonitrile-$d_3$ were refluxed with $P_2O_5$, benzene and benzene-$d_6$ were refluxed with $CaH_2$, overnight and distilled directly into flame-dried storage tubes under dry nitrogen. All glassware, syringes, and NMR tubes were oven dried (140° C.) for more than 24 hours before they were transferred into the glove box for use. All other reagents were purchased from commercial sources and were used as received. All NMR experiments were performed using a Bruker Avance 400 MHz NMR spectrometer.

Example 1

Preparation of p-methoxyphenyliodonium diacetate p-methoxyphenyliodonium diacetate: 2.34 g (10 mmol) p-iodoanisole was dissolved in 90 mL of glacial acetic acid. The solution was stirred, heated to 40° C. and 13.6 g (110 mmol) sodium perborate tetrahydrate was added gradually over an hour. The reaction mixture was kept at 40° C. for 8 hours before being cooled to room temperature. Half of the acetic acid (~45 mL) was removed and 100 mL of D.I. water was added. 3×40 mL dichloromethane was used to extract the aqueous solution. The combined organic layers were dried over sodium sulfate and solvent was evaporated to give 2.25 g (64%) of p-methoxyiodonium diacetate, which was dried in vacuo and used without further purification. o-methoxyphe-

42 nyliodonium diacetate (65%), m-cyanohenyliodonium diacetate (70%), m-trifluoromethyliodnium diacetate (80%), and 2,6-dimethoxyphenyliodoniu diacetate (83%) were synthesized using a similar procedure from corresponding iodoarenes.

Example 2

Preparation of bis(p-methoxyphenyl)iodonium trifluoroacetate

Bis(p-methoxyphenyl)iodonium trifluoroacetate: Under $N_2$ protection, 1.41 g (4 mmol) p-methoxyphenyliodonium diacetate was dissolved in 30 mL of dry dichloromethane and the solution was cooled to −30° C. 0.61 mL (8 mmol) of trifluoroacetic acid was added and the solution was slowly brought back to room temperature and stirred for 30 minutes. The solution was, again, cooled to −30° C. and 0.44 mL (4 mmol) anisole was added slowly and the mixture was warmed back up to room temperature and stirred for 1 hour. The solvent was evaporated and the residual solid was recrystallized from diethylether/dichloromethane to give 1.53 g bis(p-methoxyphenyl)iodonium trifluoroacetate (71%).

Example 3

Preparation of Bis(p-methoxyphenyl)iodonium tosylate

Bis(p-methoxyphenyl)iodonium tosylate: Under $N_2$ protection, 352 mg (1 mmol) p-methoxyphenyliodonium diacetate was dissolved in 1.5 mL of dry acetonitrile. The solution was combined with a solution of 190 mg (1 mmol) tosylic acid monohydrate in 1.5 mL of dry acetonitrile. After addition of 0.11 mL (1 mmol) p-iodoanisole, the mixture was allowed to react at room temperature for 2 hours. The solvent was then removed and the remaining solid was recrystallized from diethylether/dichloromethane to give 422 mg bis(p-methoxyphenyl)iodonium tosylate (82%).

Example 4

Preparation of Bis(p-methoxyphenyl)iodonium hexafluorophosphate

Bis(p-methoxyphenyl)iodonium hexafluorophosphate: Under $N_2$ protection, 352 mg (1 mmol) p-methoxyphenyliodonium diacetate was dissolved in 1.5 mL of dry acetonitrile. The solution was combined with a solution of 190 mg (1 mmol) tosylic acid monohydrate in 1.5 mL of dry acetonitrile. After addition of 0.11 mL (1 mmol) p-iodoanisole, the mixture was allowed to react at room temperature for 2 hours. 10 mL of water was added to the reaction mixture followed by extraction with 3×5 mL hexanes. The water layer was treated with 502 mg (3 mmol) $NaPF_6$. The white precipitation was taken up in dichloromethane and recrystallization with diethylether/dichloromethane provided 391 mg bis(p-methoxyphenyl)iodonium hexafluorophosphate (80.5%).

Example 5

Preparation of Phenyl-4-methoxyphenyliodonium hexafluorophosphate

Phenyl-4-methoxyphenyliodonium hexafluorophosphate was synthesized according to the procedure described for the synthesis of bis(p-methoxyphenyl)iodonium hexafluorophosphate from the corresponding aryliodonium diacetate and anisole. (77.9%)

Example 6

Preparation of 2-methoxyphenyl-4'-methoxyphenyliodonium hexafluorophosphate 2-methoxyphenyl-4'-methoxyphenyliodonium hexafluorophosphate was synthesized according to the procedure described for the synthesis of bis(p-methoxyphenyl)iodonium hexafluorophosphate from the corresponding aryliodonium diacetate and anisole. (83.3%)

Example 7

Preparation of 3-cyanophenyl-4'-methoxyphenyliodonium hexafluorophosphate 3-cyanophenyl-4'-methoxyphenyliodonium hexafluorophosphate was synthesized according to the procedure described for the synthesis of bis(p-methoxyphenyl)iodonium hexafluorophosphate from the corresponding aryliodonium diacetate and anisole. (73.7%)

Example 8

Preparation of 3-(trifluoromethyl)phenyl-4'-methoxyphenyliodonium hexafluorophosphate 3-(trifluoromethyl)phenyl-4'-methoxyphenyliodonium hexafluorophosphate was synthesized according to the procedure described for the synthesis of bis(p-methoxyphenyl)iodonium hexafluorophosphate from the corresponding aryliodonium diacetate and anisole. (96.1%)

Example 9

Preparation of 2,6-dimethoxyphenyl-4'-methoxyphenyliodonium hexafluorophosphate 2,6-dimethoxyphenyl-4'-methoxyphenyliodonium hexafluorophosphate was synthesized according to the procedure described for the synthesis of bis(p-methoxyphenyl)iodonium hexafluorophosphate from the corresponding aryliodonium diacetate and anisole. (86%)

Example 10

Preparation of 2-Bromo-4,5-dimethoxylbenzeneethanamine

2-Bromo-4,5-dimethoxylbenzeneethanamine: Bromine (1.1 mL, 22 mmol) in acetic acid (10 mL) was slowly added into a vigorously stirred solution of 2-(3,4-dimethoxyphenyl)ethylamine (3.4 mL, 20 mmol) in 50 mL acetic acid. 2-bromo-4,5-dimethoxylbenzeneethanamine precipitated out after 15 minutes. The mixture was stirred for another two hours, filtered, and washed with dichloromethane 10 mL×3 and petroleum ether 10 mL×3. The resulting solid was taken up in water and the pH was brought to 10 with aqueous KOH solution. Extraction with dichloromethane followed by evaporation of the solvent yielded 4.12 g (78%) 2-Bromo-4,5-dimethoxylbenzeneethanamine. The crude product was dried under dynamic vacuum overnight and used without further purification.

Example 11

Preparation of 2-Bromo-4,5-dimethoxyl-(2-phthalimidoethyl)benzene

2-Bromo-4,5-dimethoxyl-(2-phthalimidoethyl)benzene: 2-Bromo-4,5-dimethoxylbenzeneethanamine (3.5 g 13.2 mmol) was dissolved and stirred in 50 mL dry acetonitrile. 2.14 mL (1.1 equiv) phthaloyl dichloride and 7 mL (3 equiv) Hünig's base were added. The mixture was stirred at room temperature overnight. Acetonitrile was then removed, and the remaining product was taken up in dichloromethane and washed with basic water (pH=11). The aqueous wash was extracted with dichloromethane 3×15 mL. The organic fractions were combined and dried over sodium sulfate. Solvent was removed to give the crude product, which was then purified by column chromatography. Calculated yield: 1.8 g (34%).

Example 12

Preparation of 3,4-dimethoxyphenyltributyltin 3,4-dimethoxyphenyltributyltin: Under $N_2$ protection, 1.085 g (5 mmol) 4-bromoveratrole and 289 mg (5 mol %) $Pd(0)(PPh_3)_4$ was dissolved in 15 mL of dry toluene, the solution was transferred into a storage tube equipped with a Teflon Chemcap Seal, and 3.19 g (5 mmol) hexabutylditin was added. The tube was sealed, heated to, and kept at 120° C. for 48 hours. The reaction mixture was allowed to cool to room temperature, and diluted with 15 mL hexane. 15 mL of saturated aqueous KF solution was added and the mixture was stirred for 30 minutes followed by filtration through celite. The organic layer was separated; solvent was removed to provide the crude product as a yellow oil. The crude was purified by column chromatography (hexane/dichloromethane 98/2, basic aluminum) to give 1.69 g (79.1%) pure 3,4-dimethoxyphenyltributyltin.

Example 13

Preparation of 3,4-dimethoxy-2-methylphenyltributyltin 3,4-dimethoxy-2-methylphenyltributyltin was synthesized in a similar fashion as described in the procedure for the synthesis of 3,4-dimethoxyphenyltributyltin from the corresponding bromo precursor. (76.2%)

Example 14

Preparation of 3,4-dimethoxy-2-(2-phthalimido)phenyltributyltin 3,4-dimethoxy-2-(2-phthalimido)phenyltributyltin was synthesized in a similar fashion as described in the procedure for the synthesis of 3,4-dimethoxyphenyltributyltin from the corresponding bromo precursor. (20%)

Example 15

3,4-dimethoxyphenyl-4'-methoxyphenyliodonium hexafluorophosphate 3,4-dimethoxyphenyl-4'-methoxyphenyliodonium hexafluorophosphate: Under $N_2$ protection, 352 mg (1 mmol)

p-methoxyphenyliodonium diacetate was dissolved in 1.5 mL of dry acetonitrile. The solution was combined with a solution of 190 mg (1 mmol) tosylic acid monohydrate in 1.5 mL of dry acetonitrile. After addition of 427 mg (1 mmol) 3,4-dimethoxyphenyltributyltin, the mixture was allowed to react at room temperature for 2 hours. 10 mL of water was added to the reaction mixture followed by extraction with 3×5 mL hexanes. The water layer was treated with 502 mg (3 mmol) $NaPF_6$. The white precipitation was taken up in dichloromethane and recrystallization with diethylether/dichloromethane provided 370 mg (71.7%) 3,4-dimethoxyphenyl-4'-methoxyphenyliodonium hexafluorophosphate.

Example 16

Preparation of 3,4-dimethoxy-2-methylphenyl-4'-methoxyphenyliodonium hexafluorophosphate 3,4-dimethoxy-2-methylphenyl-4'-methoxyphenyliodonium hexafluorophosphate was synthesized in a similar fashion as 3,4-dimethoxyphenyl-4'-methoxyphenyliodonium hexafluorophosphate from p-methoxyphenyliodonium diacetate and the corresponding aryl tin precursor. (75%)

Example 17

Preparation of 3,4-dimethoxy-2-(2-phthalimidoethyl)phenyl-4'-methoxyphenyliodonium hexafluorophosphate 3,4-dimethoxy-2-(2-phthalimidoethyl)phenyl-4'-methoxyphenyliodonium hexafluorophosphate hexafluorophosphate was synthesized in a similar fashion as 3,4-dimethoxyphenyl-4'-methoxyphenyliodonium hexafluorophosphate from p-methoxyphenyliodonium diacetate and the corresponding aryl tin precursor. (55%)

Example 18

Preparation of 2-methoxyphenyl-4'-methoxyphenyliodonium fluoride 2-methoxyphenyl-4'-methoxyphenyliodonium fluoride: Under $N_2$ protection, 97.2 mg (0.2 mmol) 2-methoxyphenyl-4'-methoxyphenyliodonium hexafluorophosphate and 17.7 mg (0.95 equiv) anhydrous tetramethylammonium fluoride (TMAF) were dissolved in 1 mL dry acetonitrile. The solvent was removed in vacuo followed by addition of 5 mL of dry benzene. The insoluble $TMAPF_6$ was removed by filtration; the solvent was again removed in vacuo to give 30.3 mg (42%) 2-methoxyphenyl-4'-methoxyphenyliodonium fluoride.

Example 19

Preparation of Phenyl-4-methoxyphenyliodonium fluoride

Phenyl-4-methoxyphenyliodonium fluoride was synthesized in a similar fashion as the procedure described for 2-methoxyphenyl-4'-methoxyphenyliodonium fluoride from corresponding hexafluorophosphate. (96%)

Example 20

Preparation of 3-cyanophenyl-4'-methoxyphenyliodonium fluoride 3-cyanophenyl-4'-methoxyphenyliodonium fluoride was synthesized in a similar fashion as the procedure described for 2-methoxyphenyl-4'-methoxyphenyliodonium fluoride from corresponding hexafluorophosphate. (25%)

Example 21

Preparation of 3-(trifluoromethyl)phenyl-4'-methoxyphenyliodonium fluoride 3-(trifluoromethyl)phenyl-4'-methoxyphenyliodonium fluoride was synthesized in a similar fashion as the procedure described for 2-methoxyphenyl-4'-methoxyphenyliodonium fluoride from corresponding hexafluorophosphate. (56%)

Example 22

Preparation of 2,6-dimethoxyphenyl-4'-methoxyphenyliodonium fluoride 2,6-dimethoxyphenyl-4'-methoxyphenyliodonium fluoride was synthesized in a similar fashion as the procedure described for 2-methoxyphenyl-4'-methoxyphenyliodonium fluoride from corresponding hexafluorophosphate. (15%)

Example 23

Preparation of 3,4-dimethoxyphenyl-4'-methoxyphenyliodonium fluoride 3,4-dimethoxyphenyl-4'-methoxyphenyliodonium fluoride was synthesized in a similar fashion as the procedure described for 2-methoxyphenyl-4'-methoxyphenyliodonium fluoride from corresponding hexafluorophosphate. (90%)

Example 24

Preparation of 3,4-dimethoxy-2-methylphenyl-4'-methoxyphenyliodonium fluoride 3,4-dimethoxy-2-methylphenyl-4'-methoxyphenyliodonium fluoride was synthesized in a similar fashion as the procedure described for 2-methoxyphenyl-4'-methoxyphenyliodonium fluoride from corresponding hexafluorophosphate. (80%)

Example 25

Preparation of 3,4-dimethoxy-2-(2-phthalimidoethyl)phenyl-4'-methoxyphenyliodonium fluoride 3,4-dimethoxy-2-(2-phthalimidoethyl)phenyl-4'-methoxyphenyliodonium fluoride was synthesized in a similar fashion as the procedure described for 2-methoxyphenyl-4'-methoxyphenyliodonium fluoride from corresponding hexafluorophosphate. (45%)

Example 26

Preparation of Bis(p-methoxyphenyl)iodonium fluoride

Bis(p-methoxyphenyl)iodonium fluoride: To a mixture of 454 mg (1 mmol) Bis(p-methoxyphenyl)iodonium trifluoroacetate and 262 mg (1 mmol) anhydrous TBAF was added 1 mL of dry tetrahydrofuran (THF). The solution was allowed to stand for 1 hour, the white precipitate was collected and washed with 3×0.5 mL THF.

Calculated yield: 288.7 mg (80.2%)

Example 27

Diaryliodonium fluoride Decomposition

In a glove box, 0.5 mL dry $d_6$-benzene was added to 0.02 mmol of the diaryliodonium fluoride, the solution/mixture was transferred to a J-Young NMR tube. The tube was heated to and kept at 140° C. for 5-15 minutes. The resulting solution was analyzed by NMR and GC for product determination.

Observed yields of thermal decompositions of the diaryliodonium fluorides prepared above are described in Table 1.

TABLE 1

| Entry | Diaryliodonium fluoride | Yield of total fluoro aromatics | Yield of ArF | Conditions |
|---|---|---|---|---|
| 1 | | 77% (94%) | 57% (80%) | benzene, 140° C., 15 min |
| | | 65% (77%) | 40% (70%) | acetonitrile 140° C., 15 min |
| 2 | | 99% (94%) | 86%* (80%) | benzene, 140° C., 18 min |
| | | 43% (38%) | 43% (38%) | acetonitrile 140° C., 18 min |
| 3 | | 82% (80%) | 49% (48%) | benzene, 140° C., 15 min |
| | | 60% (58%) | 40% (38%) | acetonitrile 140° C., 15 min |
| 4 | | 47% (44%) | 19% (17%) | benzene, 140° C., 15 min |
| | | 34% (32%) | 7% (8%) | acetonitrile 140° C., 15 min |
| 5 | | 91% (88%) | 77% (74%) | benzene, 140° C., 15 min |
| | | 38% (39%) | 30% (28%) | acetonitrile 140° C., 15 min |
| 6 | | 90% (92%) | 78% (82%) | benzene, 140° C., 11 min |
| | | 81% (78%) | 49% (48%) | acetonitrile 140° C., 11 min |

TABLE 1-continued

| Entry | Diaryliodonium fluoride | Yield of total fluoro aromatics | Yield of ArF | Conditions |
|---|---|---|---|---|
| 7 | 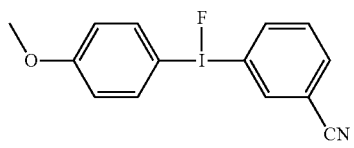 [SMILES: COc1ccc(I(F)c2cccc(C#N)c2)cc1] | 89% (90%)<br>78% (77%) | 89% (90%)<br>78% (77%) | benzene,<br>140° C., 5 min<br>acetonitrile<br>140° C., 5 min |
| 8 | 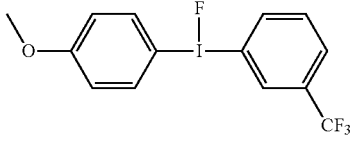 [SMILES: COc1ccc(I(F)c2cccc(C(F)(F)F)c2)cc1] | 95% (92%)<br>67% (76%) | 85% (84%)<br>68% (76%) | benzene,<br>140° C., 10 min<br>acetonitrile<br>140° C., 10 min |
| 9 | 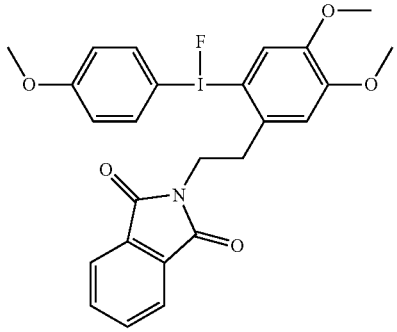 | 80% | 80%<br>(no fluoroanisole detected) | benzene,<br>140° C., 15 min |
| 10 | 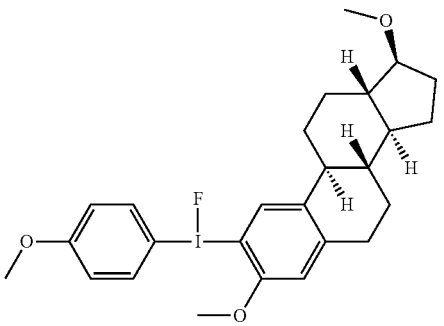 | 60% | 40% | benzene,<br>140° C., 15 min |

( ) determined by GC
*benzyne chemistry led to the formation of 3-fluoroanisole

Examples 28

Impact of Additional Salts on F-MTEB

The effect of salt present in solution during the decomposition of (3-cyano-5-((2-methylthiazol-4-yl)ethynyl)phenyl) (4-methoxyphenyl)iodonium triflate (Ar-MTEB-OTf) was examined at 90° C. in benzene and acetonitrile. Each solvent was tested in the absence of salt, presence of 1 equivalent of salt, and presence of 2 equivalents of salt. The preparation of each reaction condition is summarized below. A TMAF stock solution of 3.3 mg/mL in dry, degassed acetonitrile was prepared for addition to each reaction tube.

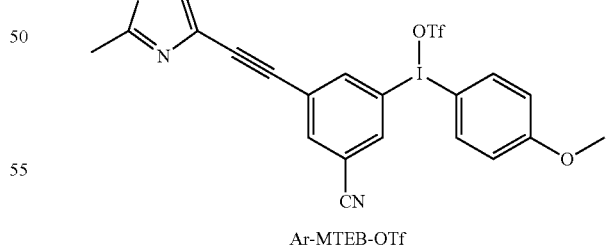

Ar-MTEB-OTf

Acetonitrile No Salt

Iodonium triflate precursor (0.004 g, 6.6 µmol) was dissolved in 0.38 mL of dry, degassed acetonitrile, under nitrogen atmosphere, with 18 µL of TMAF (6.6 µmol) stock solution. Next, 0.4 mL of dry, degassed benzene was added to the residue and passed twice through 0.22 µm PTFE membrane filter. The solution was again subjected to vacuum to remove solvent and the remaining residue was dissolved in 0.4 mL of dry, degassed $d_3$-acetonitrile. The reaction mixture was placed in a silicon oil bath and monitored at 90° C.

Acetonitrile+1 eq. TMAOTf

Under nitrogen atmosphere, iodonium triflate precursor (0.004 g, 6.6 μmol) was dissolved in 0.38 mL dry, degassed $d_3$-acetonitrile, and combined with 18 μL of TMAF (6.6 μmol) stock solution. The reaction mixture was placed in silicon oil bath and monitored at 90° C.

Acetonitrile+2 eq. TMAOTf

Under nitrogen atmosphere, iodonium triflate precursor (0.004 g, 6.6 μmol) was dissolved in 0.38 mL dry, degassed $d_3$-acetonitrile and combined with 18 μL of TMAF (6.6 μmol) stock solution, with a subsequent addition of tetramethylammonium triflate (0.0015 g, 6.6 μmol) to the reaction mixture. The solution was then placed in a silicon oil bath and monitored at 90° C.

Benzene No Salt

Under nitrogen atmosphere, iodonium triflate precursor (0.004 g, 6.6 μmol) was dissolved in 0.38 mL dry degassed acetonitrile and combined with 18 μL of TMAF (6.6 μmol) stock solution. The acetonitrile was removed by vacuum and the remaining residue was redissolved in 0.4 mL dry, degassed $d_6$-benzene. The solution was passed twice through 0.22 μm PTFE filter, sealed under nitrogen, and monitored in silicon oil bath at 90° C.

Benzene+1 eq. TMAOTf

Under nitrogen atmosphere, iodonium triflate precursor (0.004 g, 6.6 μmol) was dissolved in 0.38 mL dry, degassed acetonitrile and combined with 18 μL of TMAF (6.6 μmol) stock solution. The acetonitrile was removed by vacuum and the remaining residue was redissolved in 0.4 mL dry, degassed $d_6$-benzene. The reaction mixture was sealed under nitrogen and monitored in silicon oil bath at 90° C.

Benzene+2 eq. TMAOTf

Under nitrogen atmosphere, iodonium triflate precursor (0.004 g, 6.6 μmol) was dissolved in 0.38 mL dry, degassed $d_3$-acetonitrile and combined with 18 μL of TMAF (6.6 μmol) stock solution, with a subsequent addition of tetramethylammonium triflate (0.0015 g, 6.6 μmol) to the reaction mixture. The acetonitrile was removed by vacuum and the remaining residue was redissolved in 0.4 mL $d_6$-benzene. The solution was then placed in a silicon oil bath and monitored at 90° C.

Figure 2:
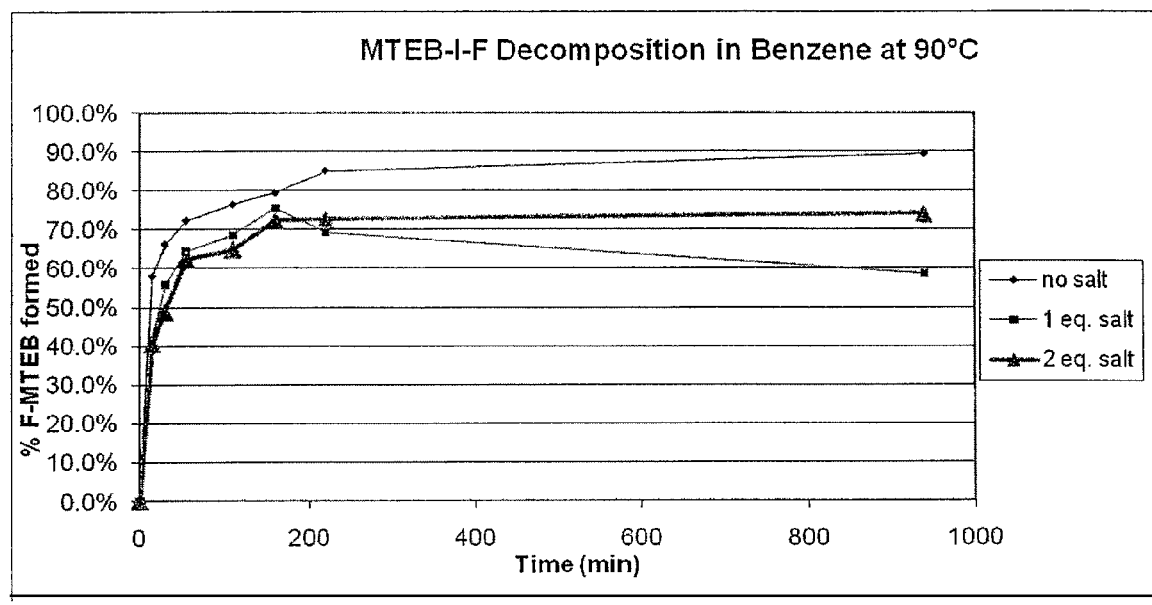
FIG. 2 shows the decomposition of MTEB-I-F in benzene at 90° C.

The results of these experiments are shown in FIGS. 1 and 2. It is clear that added salt has a large negative impact on the yield of the reaction in acetonitrile, but not as significant an impact on the results for the decomposition reaction performed in the nonpolar solvent benzene. This latter result may be due to the fact that TMAOTf is only sparingly soluble in benzene.

Example 29

Fluorinations of Radiofluorination of MTEB under Conventional Conditions

For each reaction the iodonium precursor Ar-MTEB-OTf (2 mg) was dissolvent in 300 μL of either acetonitrile, DMF, or DMSO.

Preparation of Kryptofix 222/$K_2CO_3$ $^{18}F$ source: A mixture of 50-100 μL of [$^{18}O$]$H_2O$ with [$^{18}F$]fluoride+15 μL of 1 M $K_2CO_3$ (aq)+800 μL $CH_3CN$ was heated for 3 minutes in a microwave cell at 20 W. The mixture was treated with 800 μL of $CH_3CN$ and heated again. Excess solvent was removed under a stream of dry nitrogen at 80° C.

Run 1: A solution of Ar-MTEB-OTf (2 mg) in 300 μL DMF was added to the dried Kryptofix 222/$K_2CO_3$ $K^{18}F$ source and heated in a microwave (50 W, 1.5 min). No detectable radiolabeled MTEB was seen by radio-TLC. Additional microwave heating for 3 or 6 minutes resulted in no $^{18}F$-MTEB.

Run 2: A solution of Ar-MTEB-OTf (2 mg) in 300 μL DMSO was added to the dried Kryptofix 222/$K_2CO_3$ $K^{18}F$ source and heated in a conventional oil bath at 120° C. for 15 minutes. No detectable radiolabeled MTEB was seen by radio-TLC. Further heating for 15 or 30 minutes resulted in the formation of no detectable $^{18}F$-MTEB.

For runs 3 and 4, a solution of [$^{18}F$]TBAF was prepared by addition of TBAOH to the [$^{18}O$]$H_2O$ solution containing [$^{18}F$]fluoride. Drying was performed in vacuo. The resulting solid was treated with 800 μL of $CH_3CN$ and dried by heating to 80° C. under a stream of dry nitrogen.

Run 3: A solution of Ar-MTEB-OTf (2 mg) in 300 μL DMF was added to the [$^{18}F$]TBAF and heated in at 150° C. oil bath for 15 minutes, 30 minutes, and one hour. No detectable radiolabeled MTEB was seen by radio-TLC.

Run 6: A solution of Ar-MTEB-OTf (2 mg) in 300 μL DMSO was added to the [$^{18}F$]TBAF and heated in at 120° C. oil bath for 15 minutes, 30 minutes, and one hour. A yield of 6.3% of radiolabeled MTEB was seen by radio-TLC.

Example 30

Preparation of $^{18}F$-MTEB with Salt Removal

[$^{18}F$]TBAF was dried twice with MeCN at 90° C. under reduced pressure (-10 mmHg). Ar-MTEB-OTf (2 mg) was dissolved in MeCN (300 μL) and added to the vial containing the dried [$^{18}F$]TBAF. The reaction mixture was stirred at 90° C. and the MeCN was evaporated under reduced pressure (-10 mm Hg). The remaining residue was re-dissolved in 2 mL of dry benzene, passed through 0.22-mm syringe filter, and heated to 100° C. for 20 minutes (radiochemical yield (RCY)=ca 70%, determined by radio-HPLC and radio-TLC)

Example 31

Preparation of $^{18}F$-MTEB with Salt Removal

[$^{18}F$]TBAF was dried twice with MeCN at 90° C. under reduced pressure (-10 mmHg). Ar-MTEB-OTf (2 mg) was dissolved in MeCN (300 μL) and added to the vial containing the dried [$^{18}F$]TBAF. The reaction mixture was stirred at 90° C. and the MeCN was evaporated under reduced pressure (-10 mm Hg). The remaining residue was re-dissolved in 2 mL of dry benzene, passed through 0.22-mm syringe filter, and heated to 130° C. for 20 minutes (radiochemical yield (RCY)=ca 90%, determined by radio-HPLC and radio-TLC)

Example 32

Preparation of [$^{18}F$]-6-Fluoro-L-DOPA

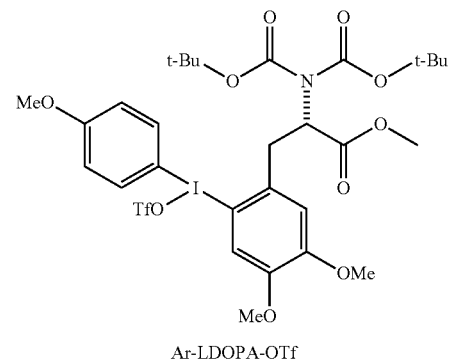 [SMILES: COC(=O)[C@H](Cc1cc(OC)c(OC)cc1I(OS(=O)(=O)C(F)(F)F)c1ccc(OC)cc1)N(C(=O)OC(C)(C)C)C(=O)OC(C)(C)C]

Ar-LDOPA-OTf

Ar-LDOPA-OTf (2 mg) is dissolved in 300 μL of dry acetonitrile and added to a vial containing dry [$^{18}$F]TBAF. The solution is warmed to 90° C. and the solvent is removed under reduced pressure. Dry toluene (500 μL) is added to the residue and the solution is passed through a 0.22 μm PTFE membrane filter and heated (in a sealed vessel) to 130° C. for 20 minutes. The solvent is removed under reduced pressure and the residue is treated with 48% HBr (500 μL) and heated at 140° C. for 8 minutes to remove the protecting groups. The [$^{18}$F]-6-Fluoro-L-DOPA is purified by reverse phase chromatography.

Example 33

General Procedure for the Preparation of Fluorinated Aryl Amino Acids and Their Derivatives The appropriate (4-methoxyphenyl)aryliodonium triflate (2-3 mg) is dissolved in 300 μL of dry acetonitrile and added to a vial containing dry [$^{18}$F]TBAF. The solution is warmed to 90° C. and the solvent is removed under reduced pressure. Dry toluene or benzene (500 μL) is added to the residue and the solution is passed through a 0.22 μm PTFE membrane filter and heated (in a sealed vessel) to 130° C. for 20 minutes. The solvent is removed under reduced pressure and the residue is treated with 48% HBr (500 μL) and heated at 140° C. for 8 minutes to remove the protecting groups. The [$^{18}$F]-fluorinated aryl amino acid or derivative is purified by reverse phase chromatography.

Example 34

Preparation of 6-Fluoro-L-DOPA

Figure 3:
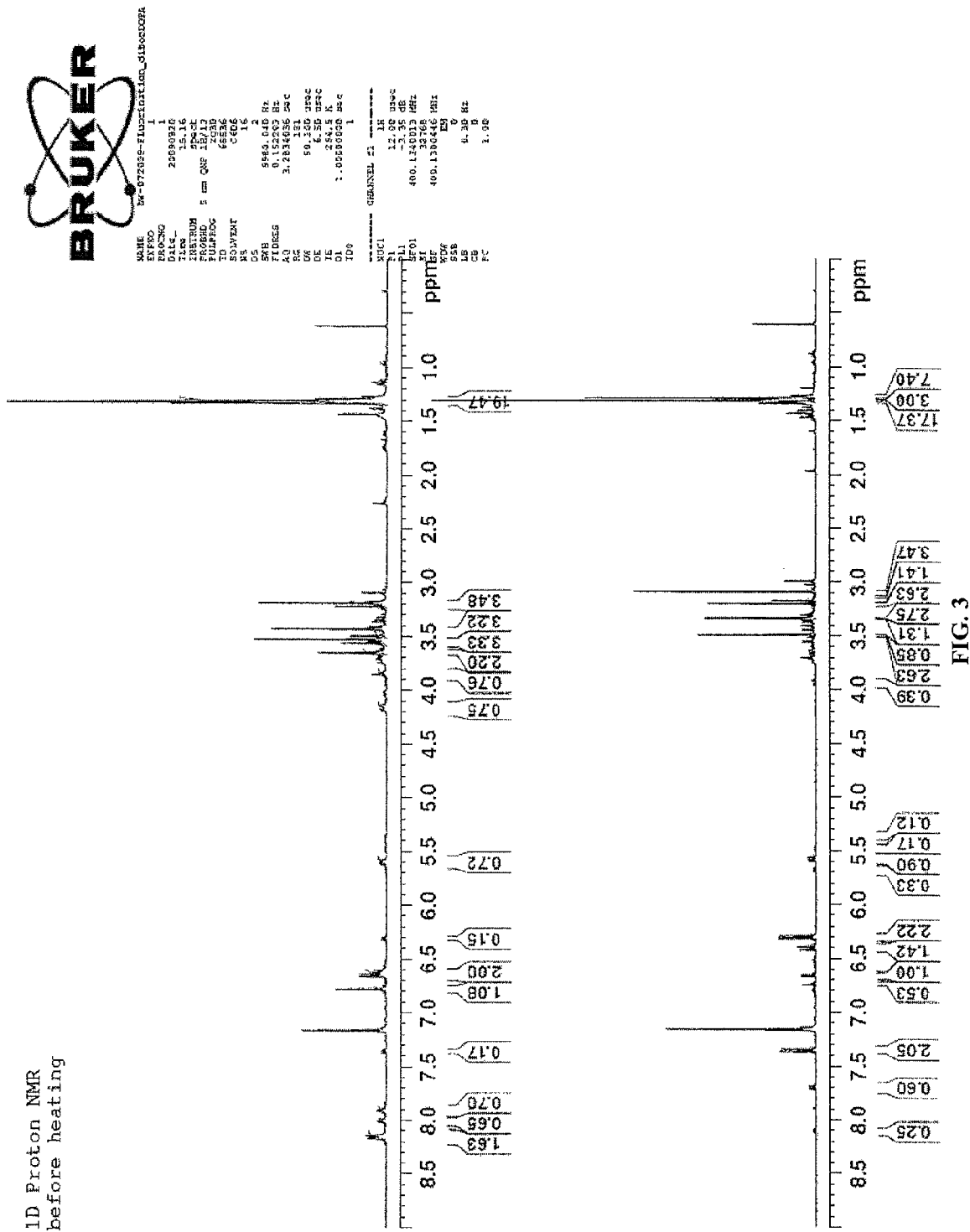
FIG. 3 details the $^1$H NMR of 6-Fluoro-L-DOPA
FIG. 4 details the $^{19}$F NMR of 6-Fluoro-L-DOPA.
Figure 4:
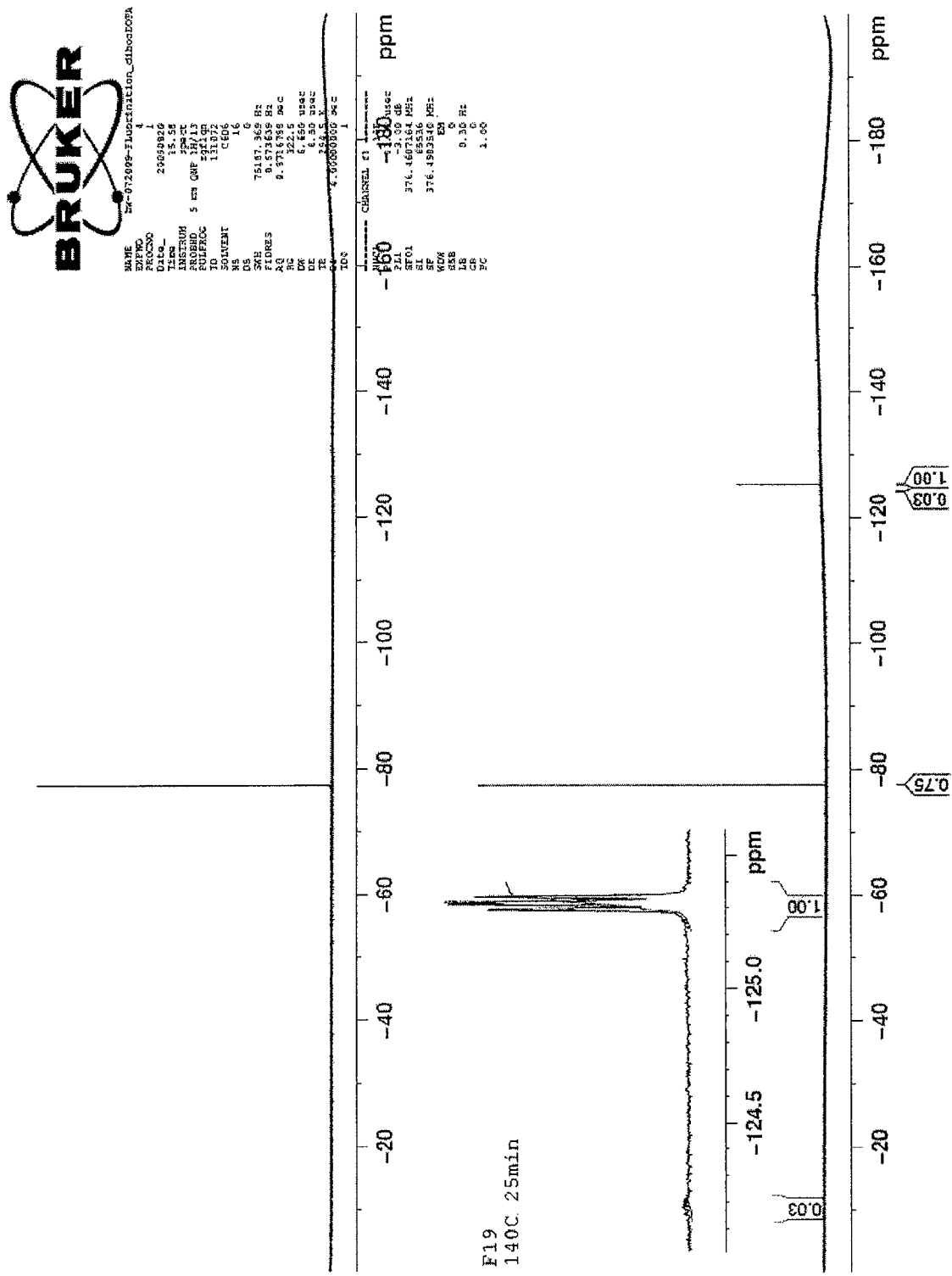

The precursor Ar-LDOPA-OTf (20 mg) was dissolved in 0.7 mL of dry CD$_3$CN and treated with one equivalent of TMAF. The solvent was removed and the residue was dissolved in 0.7 mL of d$_6$-benzene, placed in an NMR tube equipped with a PTFE valve, and heated to 140° C. for 20 minutes. $^1$H and $^{19}$F NMR spectra (FIGS. 3 and 4) indicated that the yield of the reaction was 85% and that the yield of 4-fluoroanisole was approximately 1%.

Example 35

Deprotection of 6-Fluoro-L-DOPA

The solvent was removed from the reaction mixture containing crude 6-fluoro-L-DOPA (Example 34). The residue was dissolved in 1 mL of 48% aqueous HBr and the solution was heated to 140° C. for 10 minutes. The solution was neutralized with sodium bicarbonate and the water was evaporated. $^1$H and $^{19}$F NMR spectra (D$_2$O) were identical to the authentic standard, as was confirmed by adding independently obtained 6-fluoro-L-DOPA to the NMR tube.

A number of embodiments of the invention have been described. Nevertheless, it will be understood that various modifications may be made without departing from the spirit and scope of the invention. Accordingly, other embodiments are within the scope of the following claims.

What is claimed is:

1. A method for making a compound of Formula (3):

wherein:
Ar$^2$ is an aryl or heteroaryl ring system;
the method comprising reacting in a polar solvent a compound MF, wherein M is a counter ion, and a compound of Formula (2):

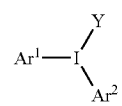

wherein:
Ar$^1$ is an electron rich aryl or heteroaryl ring system;
Y is a leaving group; and
Ar$^2$ is as defined above;
removing the polar solvent from the reaction mixture; and
heating a solution comprising the remaining mixture and a nonpolar solvent.

2. A method for making a compound of Formula (3):

wherein:
Ar$^2$ is an aryl or heteroaryl ring system;
the method comprising heating a mixture comprising a nonpolar solvent, a compound MF, wherein M is a counter ion, and a compound of Formula (2):

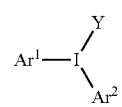

wherein:
Ar$^1$ is an electron rich aryl or heteroaryl ring system;
Y is a leaving group; and
Ar$^2$ is as defined above.

3. A method for making a compound of Formula (3):

wherein:
Ar$^2$ is an aryl or heteroaryl ring system;
the method comprising reacting in a polar solvent a compound MF, wherein M is a counter ion, and a compound of Formula (2):

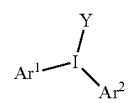

wherein:
Ar$^1$ is an electron rich aryl or heteroaryl ring system;
Y is a leaving group; and
Ar$^2$ is as defined above;
removing the polar solvent from the reaction mixture;
combining the remaining mixture with a nonpolar solvent;
filtering the resulting mixture to remove insoluble material; and
heating the filtrate.

4. A method for making a compound of Formula (3):

Ar²—F  3 wherein:

Ar² is an aryl or heteroaryl ring system;

the method comprising reacting in a nonpolar solvent a compound MF, wherein M is a counter ion, and a compound of Formula (2):

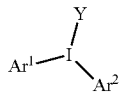  2 wherein:

Ar¹ is an electron rich aryl or heteroaryl ring system;

Y is a leaving group; and

Ar² is as defined above;

filtering the reaction mixture to remove insoluble material; and heating the filtrate.

5. The method of any one of claims 1-4, wherein Ar¹—H is more easily oxidized than benzene.

6. The method of any one of claims 1-4, wherein X is a radioactive isotope.

7. The method of any one of claims 1-4, wherein Ar¹ is substituted with at least one substituent having a Hammett $\sigma_p$ value of less than zero.

8. The method of claim 7, wherein the substituent is chosen from:

—($C_1$-$C_{10}$)alkyl, —($C_1$-$C_{10}$)haloalkyl, ($C_2$-$C_{10}$)alkenyl, ($C_2$-$C_{10}$)alkynyl, —O—($C_1$-$C_{10}$)alkyl, —C(O)—O—($C_1$-$C_{10}$)alkyl, aryl, and heteroaryl.

9. The method of any one of claims 1-4, wherein the F is a radioactive isotope of fluorine.

10. The method of any one of claims 1-4, wherein Ar¹ and Ar² are the same.

11. The method of any one of claims 1-4, wherein Ar¹ is:

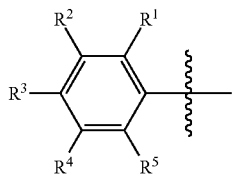

wherein:

$R^1$, $R^2$, $R^3$, $R^4$, and $R^5$ are independently chosen from: H, —($C_1$-$C_{10}$)alkyl, —($C_1$-$C_{10}$)haloalkyl, ($C_2$-$C_{10}$)alkenyl, ($C_2$-$C_{10}$)alkynyl, —O—($C_1$-$C_{10}$)alkyl, —C(O)—O—($C_1$-$C_{10}$)alkyl, aryl, and heteroaryl, or two or more of $R^1$, $R^2$, $R^3$, $R^4$, and $R^5$ come together to form a fused aryl or heteroaryl ring system.

12. The method of any one of claims 1-4, wherein Ar² is chosen from a phenylalanine derivative, tyrosine derivative, typtophan derivative, histidine derivative, and an estradiol derivative.

13. The method of any one of claims 1-4, wherein Ar² is chosen from:

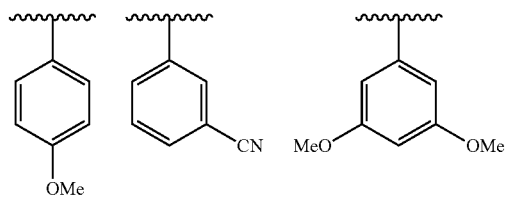

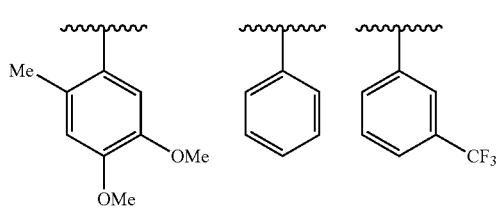

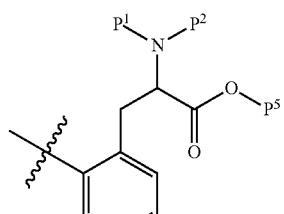

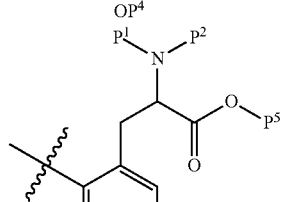

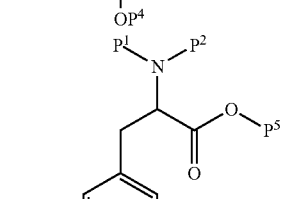

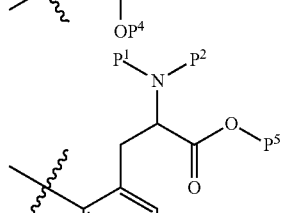

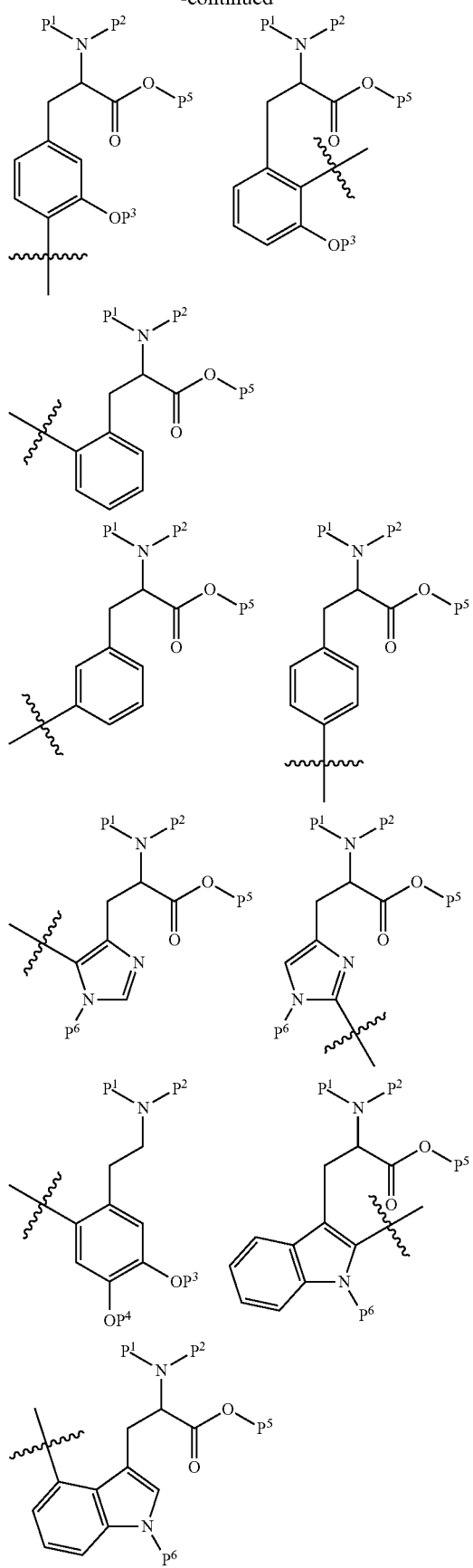
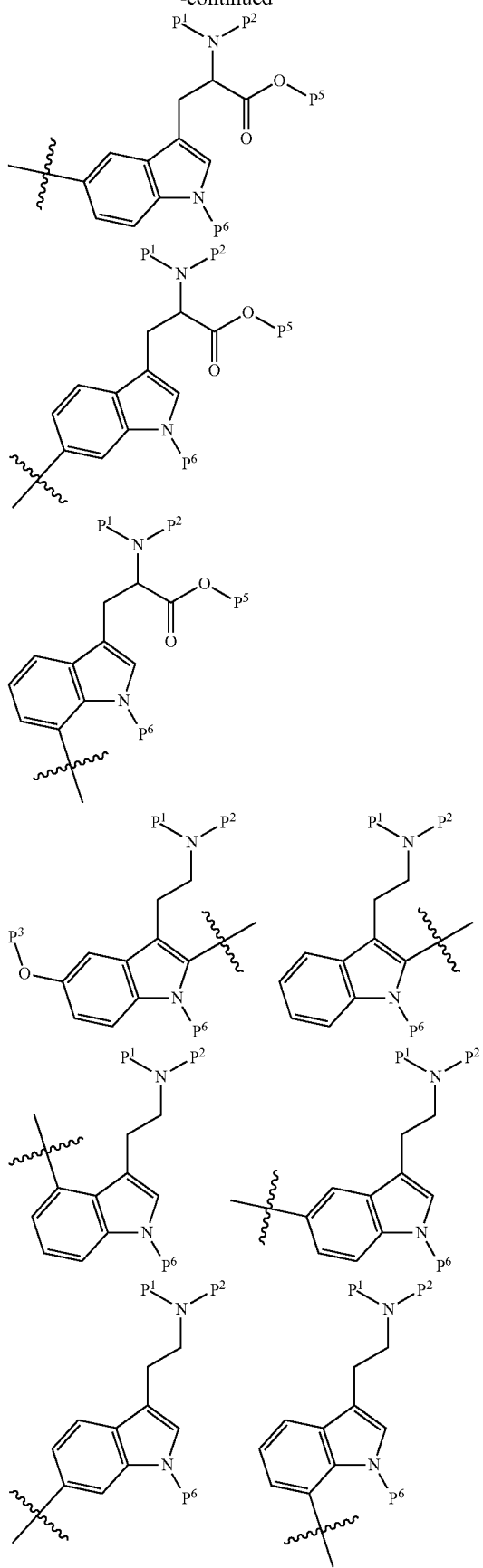

-continued
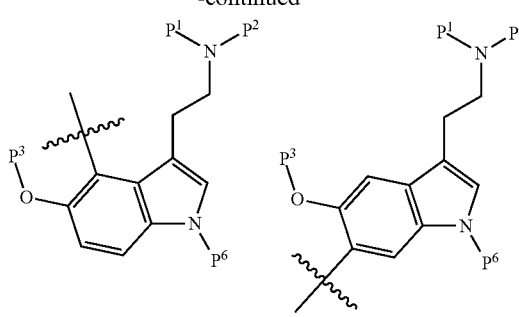
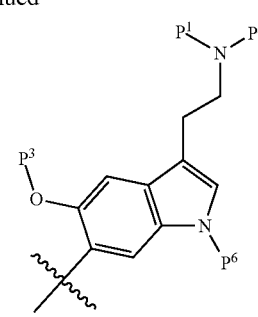
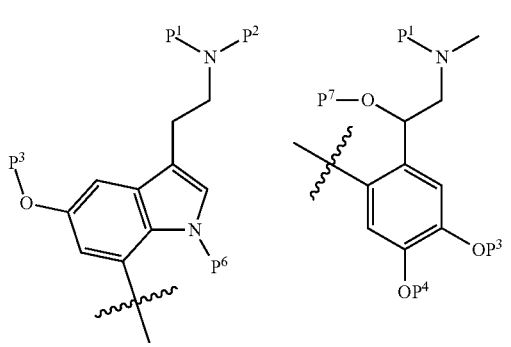
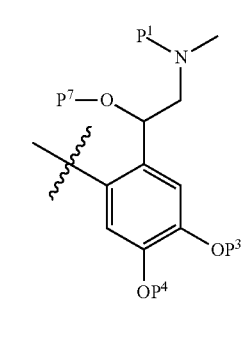
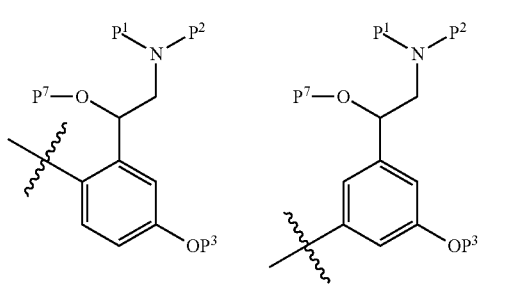
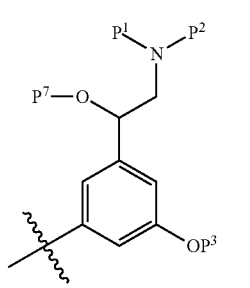
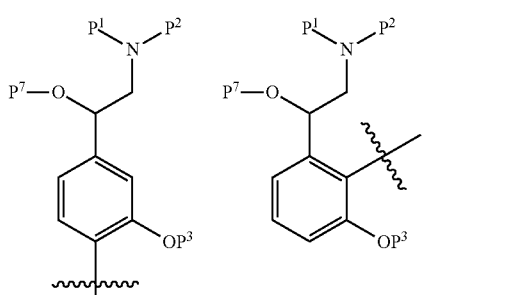
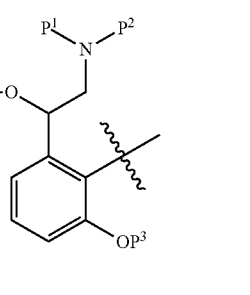
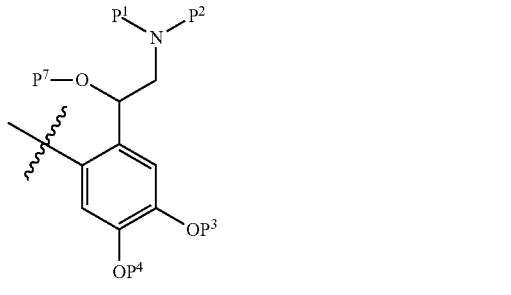
-continued
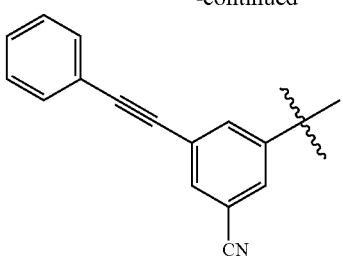
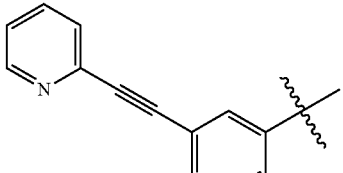
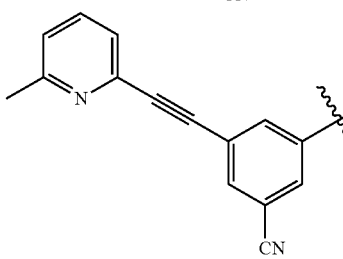
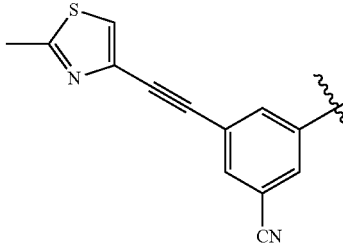
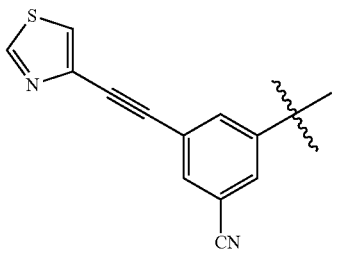
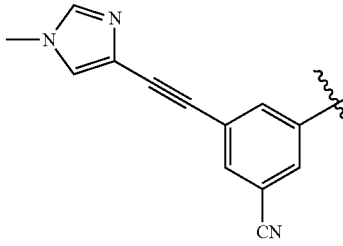
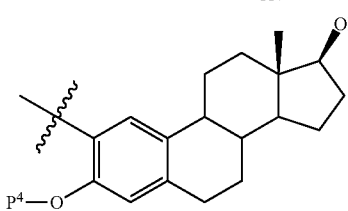

-continued

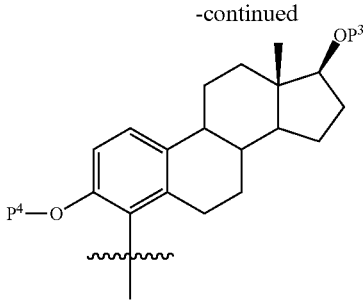

wherein:
each of $P^1$, $P^2$ and $P^6$ are independently a nitrogen protecting group, or $P^1$ and $P^2$ come together to form a single nitrogen protecting group;
each of $P^3$, $P^4$ and $P^7$ are independently an alcohol protecting group, or $P^3$ and $P^4$ come together to form a single oxygen protecting group; and
$P^5$ is a carboxylic acid protecting group.

14. The method of any one of claims 1-4, wherein the nonpolar solvent is chosen from: benzene, toluene, o-xylene, m-xylene, p-xylene, ethyl benzene, carbon tetrachloride, hexane, cyclohexane, fluorobenzene, chlorobenzene, nitrobenzene, and mixtures thereof.

15. The method of claim 14, wherein the nonpolar solvent comprises benzene.

16. The method of claim 14, wherein the nonpolar solvent comprises toluene.

17. The method of any one of claims 1-4, wherein the heating comprises heating at a temperature ranging from about 25° C. to about 250° C.

18. The method of claim 17, wherein the heating occurs for from about 1 second to about 25 minutes.

19. The method of claim 17, wherein the heating is accomplished by a flash pyrolysis method, a conventional heating method, or by a microwave method.

20. The method of any one of claims 1 and 2, wherein the mixture comprising the nonpolar solvent is filtered prior to heating.

21. The method of any one of claims 1 and 3, wherein the polar solvent is chosen from: acetonitrile, acetone, dichloromethane, ethyl acetate, tetrahydrofuran, dimethylformamide, 1,2-difluorobenzene, benzotrifluoride and mixtures thereof.

22. The method of any one of claims 1-4, wherein Y is chosen from triflate, mesylate, nonaflate, hexaflate, tosylate, nosylate, brosylate, perfluoroalkyl sulfonate, tetraphenylborate, hexafluorophosphate, trifluoroacetate, tetrafluoroborate, perchlorate, perfluoroalkylcarboxylate, chloride, bromide, and iodide.

23. The method of any one of claims 1-4, wherein M is chosen from: potassium, sodium, cesium, complexes of lithium, sodium, potassium, or cesium with cryptands or crown ethers, tetrasubstituted ammonium cations, and phosphonium cations.

24. The method of any one of claims 3 and 4, wherein the insoluble material comprises insoluble salts.

25. The method of any one of claims 3 and 4, wherein the solvent is removed from the filtrate prior to heating.

26. The method of any one of claims 1-4, wherein the compound of Formula (2) is chosen from:

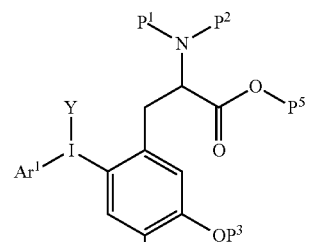

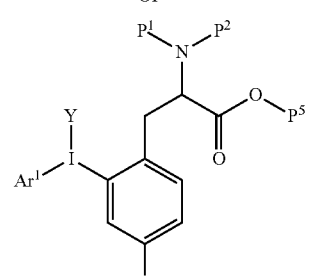

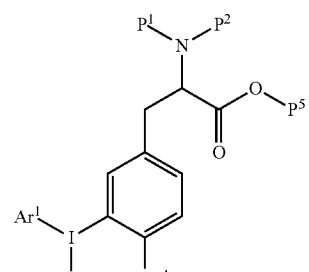

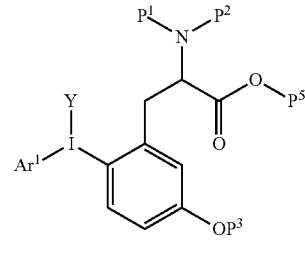 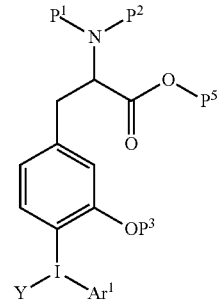

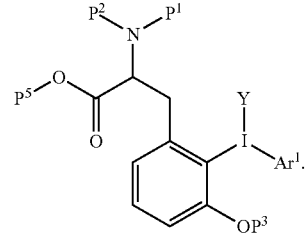

wherein:
each of $P^1$ and $P^2$ are independently a nitrogen protecting group, or $P^1$ and $P^2$ come together to form a single nitrogen protecting group;
each of $P^3$, and $P^4$ are independently an alcohol protecting group, or $P^3$ and $P^4$ come together to form a single oxygen protecting group; and
$P^5$ is a carboxylic acid protecting group.

27. The method of any one of claims 1-4, wherein the compound of Formula (3) is chosen from:

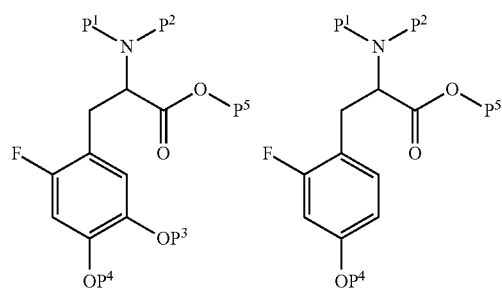

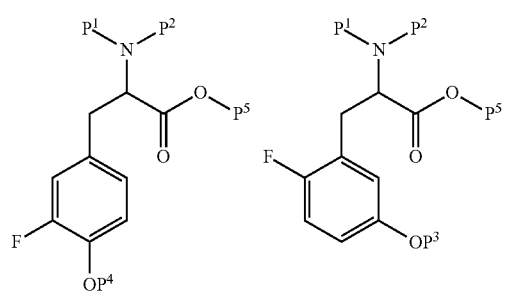

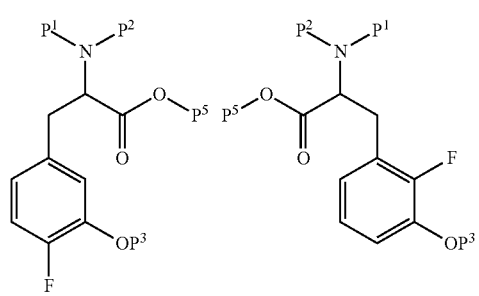

wherein:
each of $P^1$ and $P^2$ are independently a nitrogen protecting group, or $P^1$ and $P^2$ come together to form a single nitrogen protecting group;
each of $P^3$, and $P^4$ are independently an alcohol protecting group, or $P^3$ and $P^4$ come together to form a single oxygen protecting group; and
$P^5$ is a carboxylic acid protecting group.

28. The method of any one of claims 1-4, wherein the compound of Formula (2) is chosen from:

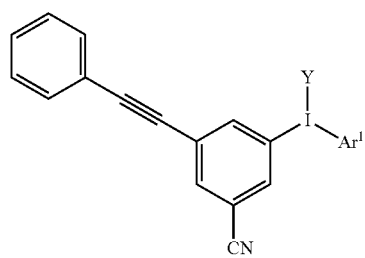

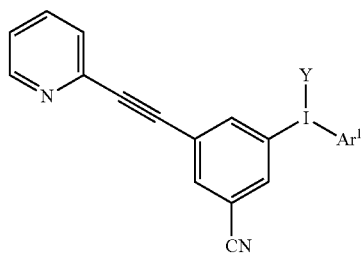

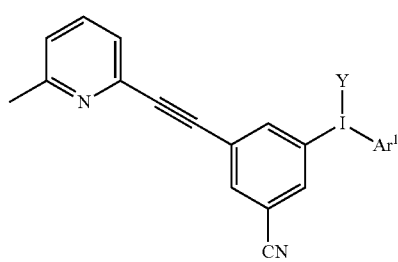

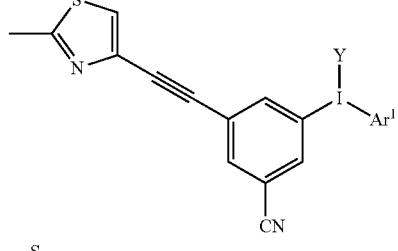

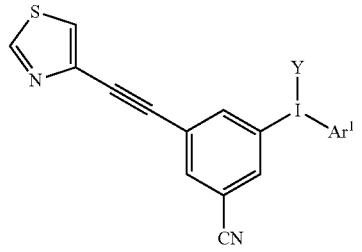

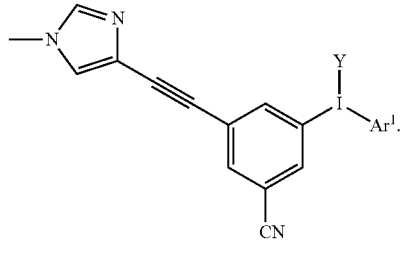

29. The method of any one of claims 1-4, wherein the compound of Formula (3) is chosen from:

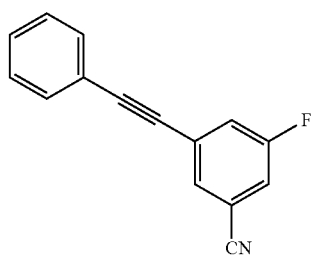

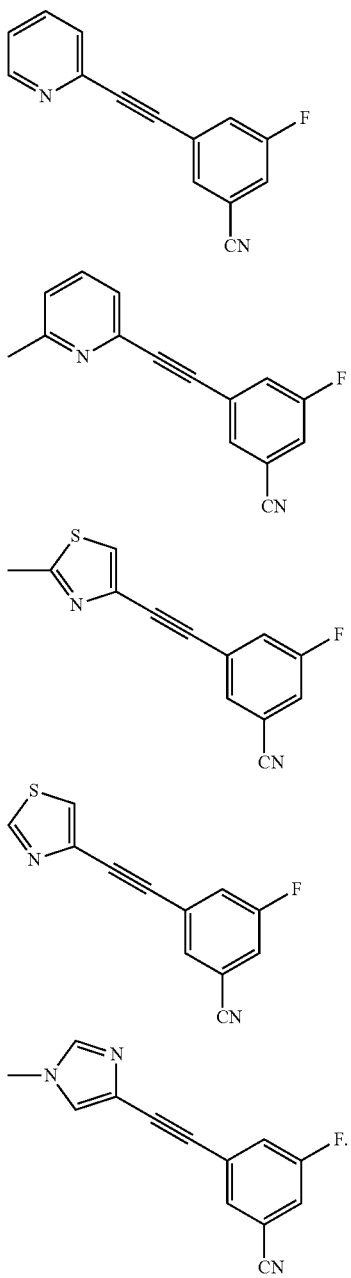

30. The method of any one of claims 1-4, wherein the compound of Formula (2) is chosen from:

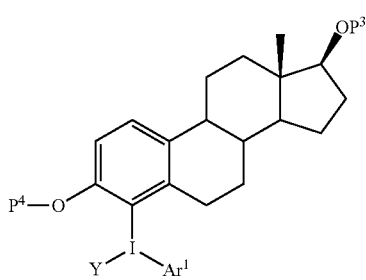

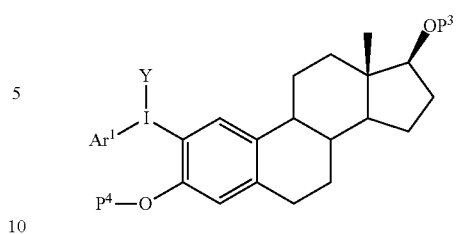

wherein:
each of P³ and P⁴ are independently an alcohol protecting group.

31. The method of any one of claims 1-4, wherein the compound of Formula (3) is chosen from:

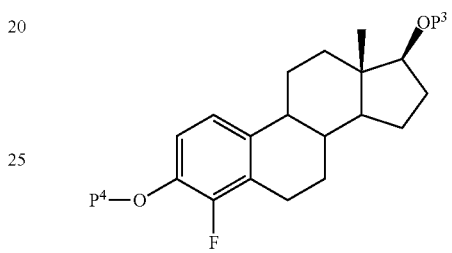

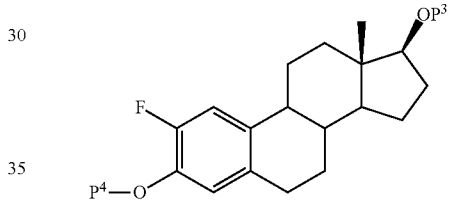

wherein:
each of P³ and P⁴ are independently an alcohol protecting group.

32. The method of any one of claims 1-4, wherein the compound of Formula (2) is:

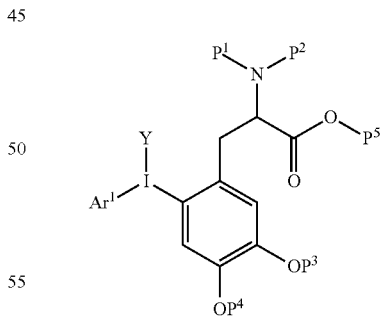

wherein:
each of P¹ and P² are independently a nitrogen protecting group, or P¹ and P² come together to form a single nitrogen protecting group;
each of P³, and P⁴ are independently an alcohol protecting group, or P³ and P⁴ come together to form a single oxygen protecting group; and
P⁵ is a carboxylic acid protecting group.

33. The method of claim 32, wherein the compound of Formula (2) is:

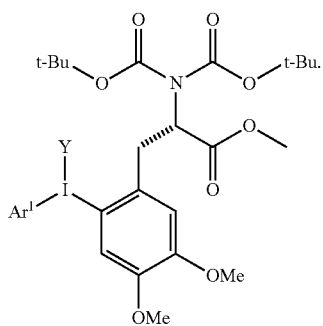

34. The method of claim 32, wherein the compound of Formula (2) is:

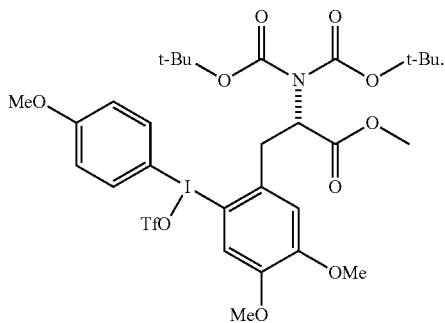

35. The method of any one of claims 1-4, wherein the compound of Formula (3) is:

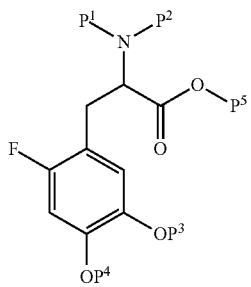

wherein:

each of $P^1$ and $P^2$ are independently a nitrogen protecting group, or $P^1$ and $P^2$ come together to form a single nitrogen protecting group;

each of $P^3$, and $P^4$ are independently an alcohol protecting group, or $P^3$ and $P^4$ come together to form a single oxygen protecting group; and $P^5$ is a carboxylic acid protecting group.

36. The method of claim 35, wherein the compound of Formula (3) is:

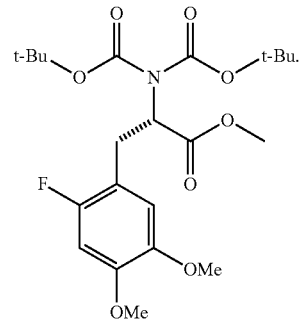

37. The method of any one of claims 1-4, wherein the compound of Formula (3) is:

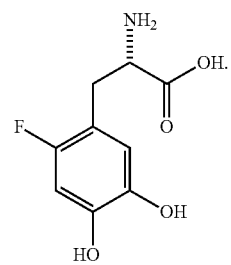

* * * * *

UNITED STATES PATENT AND TRADEMARK OFFICE
CERTIFICATE OF CORRECTION

| | | |
|---|---|---|
| PATENT NO. | : 8,604,213 B2 | Page 1 of 2 |
| APPLICATION NO. | : 13/125209 | |
| DATED | : December 10, 2013 | |
| INVENTOR(S) | : Stephen DiMagno | |

It is certified that error appears in the above-identified patent and that said Letters Patent is hereby corrected as shown below:

On the Title Page, item (56):

Column 2, First Page, Line 2 (Other Publications), please delete "flourobenzene" and insert -- fluorobenzene --, therefor.

Column 1, Page 2, Line 43 (Other Publications), please delete "(heptafluoroproyl)" and insert -- (heptafluoropropyl) --, therefor.

Column 2, Page 2, Line 66 (Other Publications), please delete "reaction f cyclic" and insert -- reaction of cyclic --, therefor.

Column 2, Page 3, Lines 26-27 (Other Publications), please delete "alph-Phyenyl" and insert -- alpha-Phenyl --, therefor.

Column 2, Page 3, Line 39 (Other Publications), please delete "diphenyloidonium" and insert -- diphenyliodonium --, therefor.

Column 2, Page 3, Line 43 (Other Publications), please delete "UUSR." and insert -- USSR. --, therefor.

Column 2, Page 3, Lines 48-49 (Other Publications), please delete "Reactions o fDiaryliodonium" and insert -- Reactions of Diaryliodonium --, therefor.

Column 1, Page 4, Line 11 (Other Publications), please delete "susbtitution" and insert -- substitution --, therefor.

Column 2, Page 4, Line 1 (Other Publications), please delete "Iodene" and insert -- Iodine --, therefor.

Signed and Sealed this
Twenty-fourth Day of June, 2014

Michelle K. Lee
*Deputy Director of the United States Patent and Trademark Office*

CERTIFICATE OF CORRECTION (continued)

Column 2, Page 4, Line 27 (Other Publications), please delete "Phenyltributystanne" and insert -- Phenyltributylstannane --, therefor.

In the Specification:

Column 1, Line 15, After "herein" insert -- . --.

In the Claims:

Column 55, Line 66 (Claim 12), please delete "typtophan" and insert -- tryptophan --, therefor.

Column 59, Line 17 (Claim 13), please delete " 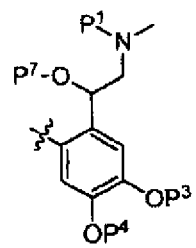 " and insert -- 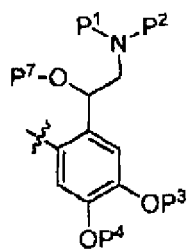 --, therefor.

Column 62, Line 52 (Claim 26), please delete the "." after the structure.

UNITED STATES PATENT AND TRADEMARK OFFICE
CERTIFICATE OF CORRECTION

PATENT NO.       : 8,604,213 B2
APPLICATION NO. : 13/125209
DATED            : December 10, 2013
INVENTOR(S)      : Stephen Dimagno It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 123 days.

Signed and Sealed this
Twenty-third Day of May, 2017

Michelle K. Lee
*Director of the United States Patent and Trademark Office*